US011299528B2

(12) United States Patent
Lee et al.

(10) Patent No.: US 11,299,528 B2
(45) Date of Patent: *Apr. 12, 2022

(54) LONG ACTING TRAIL RECEPTOR AGONISTS FOR TREATMENT OF AUTOIMMUNE DISEASES

(71) Applicant: D&D Pharmatech Inc., Seongnam-Si (KR)

(72) Inventors: Kang Choon Lee, Seoul (KR); Ha Na Eom, Gyeonggi-do (KR)

(73) Assignee: D&D PHARMATECH INC., Seongnam-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/645,276

(22) Filed: Mar. 11, 2015

(65) Prior Publication Data

US 2015/0259397 A1    Sep. 17, 2015

Related U.S. Application Data

(60) Provisional application No. 61/951,393, filed on Mar. 11, 2014.

(51) Int. Cl.
| | | |
|---|---|---|
| *C07K 14/705* | (2006.01) | |
| *A61K 38/17* | (2006.01) | |
| *A61K 45/06* | (2006.01) | |
| *A61K 39/395* | (2006.01) | |
| *A61K 47/60* | (2017.01) | |

(52) U.S. Cl.
CPC ...... *C07K 14/70575* (2013.01); *A61K 38/177* (2013.01); *A61K 39/3955* (2013.01); *A61K 45/06* (2013.01); *A61K 47/60* (2017.08); *C07K 2319/00* (2013.01); *C07K 2319/73* (2013.01)

(58) Field of Classification Search
None
See application file for complete search history.

(56) References Cited

U.S. PATENT DOCUMENTS

| | | | |
|---|---|---|---|
| 5,763,223 A | 6/1998 | Wiley | |
| 6,072,047 A | 6/2000 | Rauch | |
| 6,329,148 B1 | 12/2001 | Rosen | |
| 6,908,963 B2 | 6/2005 | Roberts | |
| 7,060,272 B2 | 6/2006 | Jian | |
| 7,160,924 B2 | 1/2007 | Kinstler | |
| 7,186,699 B2 | 3/2007 | Harding | |
| 7,368,295 B2 | 5/2008 | Tovar | |
| 7,521,056 B2 | 4/2009 | Chang | |
| 7,534,866 B2 | 5/2009 | Chang | |
| 7,550,143 B2 | 6/2009 | Chang | |
| 7,615,233 B2 | 11/2009 | Yano | |
| 7,795,404 B1 | 9/2010 | Lin | |
| 7,897,730 B2 | 3/2011 | Yu | |
| 7,906,118 B2 | 3/2011 | Chang | |
| 7,994,281 B2 | 8/2011 | Tur | |
| 8,003,111 B2 | 8/2011 | Chang | |
| 8,008,261 B2 | 8/2011 | Badley | |
| 8,029,783 B2 | 10/2011 | Adams | |
| 8,034,352 B2 | 10/2011 | Chang | |
| 8,075,916 B2 | 12/2011 | Song | |
| 8,143,380 B2 | 3/2012 | Walker | |
| 8,158,129 B2 | 4/2012 | Chang | |
| 8,198,033 B2 | 6/2012 | Austin | |
| 8,282,934 B2 | 10/2012 | Chang | |
| 8,287,888 B2 | 10/2012 | Song | |
| 8,435,540 B2 | 5/2013 | Chang | |
| 8,440,787 B2 | 5/2013 | Mcmanus | |
| 8,461,311 B2 | 6/2013 | Hawkins | |
| 8,568,721 B2* | 10/2013 | Radin | A61K 31/4706 424/130.1 |
| 8,586,020 B2 | 11/2013 | Song | |
| 8,597,659 B2 | 12/2013 | Chang | |
| 8,628,801 B2 | 1/2014 | Garreta | |
| 8,673,923 B2 | 3/2014 | El-Deiry | |

(Continued)

FOREIGN PATENT DOCUMENTS

| | | |
|---|---|---|
| KR | 1020020001719 | 1/2002 |
| KR | 1020070115602 | 6/2007 |

(Continued)

OTHER PUBLICATIONS

Zemel et al., Journal of Nutrition, 138: 1047-1052, 2008.*
Jeffery et al., The Journal of Immunology, 2009, 183:5458-5467.*
Amiram, et al., "Injectable protease-operated depots of glucagon-like peptide-1 provide extended and tunable glucose control", PNAS, 110(8);2792-7 (2013).
Anel, et al., "Apo2L/TRAIL and immune regulation", Front Biosci., 12:2074-84 (2007).
Audo, et al., "The two directions of TNF-related apoptosis-inducing ligand in rheumatoid arthritis", Cytokine,63(2):81-90 (2013).
Benedict, et al., "TRAIL: not just for tumors anymore", J. Exp. Med., 209(11):1903-6 (2012).

(Continued)

*Primary Examiner* — Marianne P Allen
(74) *Attorney, Agent, or Firm* — Pabst Patent Group LLP

(57) ABSTRACT

Methods of treating an autoimmune disease such as rheumatoid arthritis, methods of increasing apoptosis of pro-inflammatory immune cells or synoviocytes, methods of increasing the quantity of the anti-inflammatory regulatory T cells, and methods of slowing the progression of inflammation in a subject include systemically administering to the subject a pharmaceutical composition including an effective amount of a TRAIL-conjugate. Preferably, the TRAIL-conjugate is effective for at least 3 days, more preferably at least 7 days, without being part of a nanocomplex that modulates the circulation half-life or release kinetics of the TRAIL-conjugate. Combination therapies including administering a second active agent, most preferably a TNF-α inhibitor, as well as pharmaceutical composition dosage units including a TRAIL-conjugate and a TNF-α inhibitor in an effective amount for a single once weekly dose for treatment of rheumatoid arthritis are also provided.

14 Claims, 6 Drawing Sheets

Specification includes a Sequence Listing.

(56) References Cited

U.S. PATENT DOCUMENTS

| | | | |
|---|---|---|---|
| 8,709,409 B2* | 4/2014 | Okuda | A61K 31/519 |
| | | | 424/130.1 |
| 8,986,684 B2* | 3/2015 | Wang | C07K 16/2803 |
| | | | 424/130.1 |
| 9,017,726 B2 | 4/2015 | Song | |
| 9,102,735 B2 | 8/2015 | Govindan | |
| 9,150,846 B2 | 10/2015 | Jefferies | |
| 2002/0058029 A1* | 5/2002 | Hanna | A61K 39/39541 |
| | | | 424/131.1 |
| 2002/0061525 A1 | 5/2002 | Yelin | |
| 2002/0169123 A1 | 11/2002 | El-Deiry | |
| 2004/0005314 A1 | 1/2004 | Escandon | |
| 2004/0146896 A1 | 7/2004 | Rong | |
| 2004/0146968 A1 | 7/2004 | Chung | |
| 2004/0186051 A1 | 9/2004 | Kelley | |
| 2005/0203142 A1 | 9/2005 | Zeldis | |
| 2006/0141561 A1 | 6/2006 | Kelley | |
| 2006/0188498 A1 | 8/2006 | Ashkenazi | |
| 2006/0228352 A1 | 10/2006 | Schoenberger | |
| 2006/0286066 A1 | 12/2006 | Basran | |
| 2007/0066800 A1 | 3/2007 | Sidhu | |
| 2008/0044421 A1 | 2/2008 | Ashkenazi | |
| 2008/0199423 A1 | 8/2008 | Godowski | |
| 2008/0305038 A1 | 12/2008 | Rosenecker | |
| 2009/0022683 A1 | 1/2009 | Song | |
| 2009/0081157 A1 | 3/2009 | Kornbluth | |
| 2009/0203599 A1 | 8/2009 | Lee | |
| 2009/0203671 A1 | 8/2009 | Glaser | |
| 2009/0258017 A1 | 10/2009 | Callahan | |
| 2009/0324616 A1 | 12/2009 | Stassi | |
| 2009/0325867 A1 | 12/2009 | Cohen | |
| 2010/0068302 A1 | 3/2010 | Ramirez De Molina | |
| 2010/0105620 A1 | 4/2010 | Bowdish | |
| 2010/0209490 A1 | 8/2010 | Morita | |
| 2011/0020273 A1 | 1/2011 | Chang | |
| 2011/0038855 A1 | 2/2011 | Schoenberger | |
| 2011/0104103 A1 | 5/2011 | Heetebrij | |
| 2011/0165265 A1 | 7/2011 | Samali | |
| 2011/0200552 A1 | 8/2011 | Rodrigues Dos Reis | |
| 2011/0262455 A1 | 10/2011 | Samali | |
| 2012/0021995 A1 | 1/2012 | Bowdish | |
| 2012/0196795 A1 | 8/2012 | Xu | |
| 2013/0079280 A1 | 3/2013 | Baca | |
| 2013/0101553 A1 | 4/2013 | Kisseleva | |
| 2013/0150566 A1 | 6/2013 | Hua | |
| 2013/0195884 A1 | 8/2013 | Boutros | |
| 2013/0217091 A1 | 8/2013 | Chang | |
| 2014/0004081 A1 | 1/2014 | Cobbold | |
| 2014/0004120 A1 | 1/2014 | Ohtsuka | |
| 2014/0079722 A1 | 3/2014 | Prudent | |
| 2014/0086907 A1 | 3/2014 | Shah | |
| 2014/0096274 A1 | 4/2014 | Quax | |
| 2014/0105898 A1 | 4/2014 | Thomas | |
| 2014/0134647 A1 | 5/2014 | Benedict | |
| 2014/0135377 A1 | 5/2014 | Westermarck | |
| 2014/0161766 A1 | 6/2014 | Chang | |
| 2014/0178398 A1 | 6/2014 | Ashkenazi | |
| 2014/0206843 A1 | 7/2014 | Zhou | |
| 2015/0038511 A1 | 2/2015 | Schafer | |
| 2015/0056159 A1 | 2/2015 | Kontermann | |
| 2015/0056204 A1 | 2/2015 | Holland | |
| 2015/0174269 A1 | 6/2015 | Govindan | |
| 2015/0183875 A1 | 7/2015 | Cobbold | |
| 2015/0197730 A1 | 7/2015 | Shah | |
| 2015/0204877 A1 | 7/2015 | Westermarck | |
| 2015/0218282 A1 | 8/2015 | Shah | |
| 2015/0250896 A1 | 9/2015 | Zhao | |
| 2015/0259397 A1 | 9/2015 | Lee | |
| 2015/0284416 A1 | 10/2015 | Zhao | |
| 2015/0301058 A1 | 10/2015 | Schettini | |

FOREIGN PATENT DOCUMENTS

| | | | |
|---|---|---|---|
| KR | 1020110007362 | | 1/2011 |
| WO | 9900423 | | 1/1999 |
| WO | 0069911 | | 11/2000 |
| WO | 0122987 | | 4/2001 |
| WO | 2004001009 | | 12/2003 |
| WO | 2004022004 | | 3/2004 |
| WO | 2006028939 | | 3/2006 |
| WO | 2006107617 | | 10/2006 |
| WO | 2006107786 | | 10/2006 |
| WO | 2007046893 | | 4/2007 |
| WO | 2007075534 | | 7/2007 |
| WO | 2007102690 | | 9/2007 |
| WO | 2007145457 | | 12/2007 |
| WO | 2008120832 | | 10/2008 |
| WO | 2008130066 | | 10/2008 |
| WO | 2009058379 | | 5/2009 |
| WO | 2009126558 | | 10/2009 |
| WO | 2009140469 | | 11/2009 |
| WO | 2010093395 | | 8/2010 |
| WO | 2011025904 | | 3/2011 |
| WO | 11079293 | | 6/2011 |
| WO | 2011106707 | | 9/2011 |
| WO | WO 2014/044768 | * | 3/2014 |
| WO | 2014126537 | | 8/2014 |
| WO | 2015010615 | | 1/2015 |
| WO | 2015028850 | | 3/2015 |
| WO | 2015037000 | | 3/2015 |
| WO | 15092756 | | 6/2015 |
| WO | 2015127685 | | 9/2015 |
| WO | 2015164217 | | 10/2015 |

OTHER PUBLICATIONS

Byeon, et al., "Human serum albumin-TRAIL conjugate for the treatment of rheumatoid arthritis", Bioconjug Chem., 25(12):2212-21 (2014).

Chae, et al., "Improved antitumor activity and tumor targeting of NH(2)-terminal-specific PEGylated tumor necrosis factor-related apoptosis-inducing ligand", Mol Cancer Ther.,, 9(6):1719-29(2010).

Cuello, et al., "Synergistic induction of apoptosis by the combination of trail and chemotherapy in chemoresistant ovarian cancer cells", Gynecol Oncol., 81(3):380-90 (2001).

De Clerck, "B lymphocytes and humoral immune responses in rheumatoid arthritis", Clinical Rheumatol., 14 Suppl 2:14-8 (1995).

Fee, et al., "Size comparison between proteins PEGylated with branched and linear poly(ethylene glycol) molecules", Biotechnol Bioeng., 98(4):725-3 (2007).

Gieffers, "APG350 induces superior clustering of TRAIL receptors and shows therapeutic antitumor efficacy independent of cross-linking via $Fc^{3}$ receptors", Mol Cancer Ther., 12(12):2735-47 (2013).

Herbst, et al., "Phase I dose-escalation study of recombinant human Apo2L/TRAIL, a dual proapoptotic receptor agonist, in patients with advanced cancer", J. Clin. Oncol., 28(17):2839-46 (2010).

Jin, et al, "Effect of tumor necrosis factor-related apoptosis-inducing ligand on the reduction of joint inflammation in experimental rheumatoid arthritis", J. Pharmacol. Exp. Ther. 332(3):858-65 (2010).

Jo, et al., "Apoptosis Induced in normal human hepatocytes by tumor necrosis factor-related apoptosis-inducing ligand", Nature Med., 6(5):564-7 (2000).

Kim, et al., "PEGylated TNF-related apoptosis-inducing ligand (TRAIL) analogues: pharmacokinetics and antitumor effects", Bioconjug Chem., 22(8):1631-7 (2011a).

Kim, et al., "Ionic complex systems based on hyaluronic acid and PEGylated TNF-related apoptosis-inducing ligand for treatment of rheumatoid arthritis", Biomaterials, 31(34):9057-64 (2010).

Kim, et al. "PEGylated TNF-related apoptosis-inducing ligand (TRAIL)-loaded sustained release PLGA microspheres for enhanced stability and antitumor activity", J Control Release, 150(1):63-9 (2011b).

(56) References Cited

OTHER PUBLICATIONS

Kim, et al., "Preparation and characterization of Apo2L/TNF-related apoptosis-inducing ligand-loaded human serum albumin nanoparticles with improved stability and tumor distribution", J Pharm Sci., 100(2):482-91 (2011c).

Kim, et al., "A sulfate polysaccharide/TNF-related apoptosis-inducing ligand (TRAIL) complex for the long-term delivery of TRAIL in poly(lactic-co-glycolic acid) (PLGA) microspheres", J Pharm Pharmacol., 65(1):11-21 (2013).

Lamhamedi-Cherradi, et al., "Defective thymocyte apoptosis and accelerated autoimmune diseases in TRAIL-/- mice", Nat Immunol., 4(3):255-60 (2003).

Li, et al., "Anti-DR5 mAb ameliorate adjuvant arthritis rats through inducing synovial cells apoptosis", Exp biology Med, 234(12):1468-76 (2009).

Liu, et al., "CII-DC-AdTRAIL cell gene therapy inhibits infiltration of CII-reactive T cells and CII-induced arthritis", J Clin Invest., 112(9):1332-41 (2003).

Martinez-Lostao, et al., "Liposome-bound APO2L/TRAIL is an effective treatment in a rabbit model of rheumatoid arthritis.", Arthritis Rheum., 62(8):2272-82 (2010).

McInnes, et al., "Cytokines in the pathogenesis of rheumatoid arthritis", Nature Rev Immunol., 7(6):429-42 (2007).

Miranda-Carus, et al., "Rheumatoid arthritis synovial fluid fibroblasts express TRAIL-R2 (DR5) that is functionally active", Arthritis Rheum., 50(9):2786-93 (2004).

Song, et al., "Tumor necrosis factor-related apoptosis-inducing ligand (TRAIL) is an inhibitor of autoimmune inflammation and cell cycle progression", J Exp Med., 191(7):1095-104 (2000).

Van Der Sloot, "Designed tumor necrosis factor-related apoptosis-inducing ligand variants initiating apoptosis exclusively via the DR5 receptor", PNAS, 103(23):8634-9 (2006).

Wahl, "Increased apoptosis induction in hepatocellular carcinoma by a novel tumor-targeted TRAIL fusion protein combined with bortezomib", Hepatology, 57(2):625-36 (2013).

Wu, et al., "TRAIL and chemotherapeutic drugs in cancer therapy", Vitam Horm., 67:365-83 (2004).

Yang, et al., "Target specific hyaluronic acid-interferon alpha conjugate for the treatment of hepatitis C virus infection", Biomaterials 32(33);8722-9 (2011).

Yao, et al., "Intra-articular adenoviral-mediated gene transfer of trail induces apoptosis of arthritic rabbit synovium", Gene therapy, 10(12):1055-60 (2003).

Lee, et al., "Treatment with PEGylated TNF-related apoptosis-inducing ligand (TRAIL) induces apoptosis of human rheumatoid arthritis (RA) fibroblast-like synoviocytes (FLS) and suppresses arthritis in murine colla en-induced arthritis", Arthritis and Rheumatism; 72nd Annual scientific meeting of the American college of Rheumatology/43rd annual scientific meeting, Wiley San Francisco, CA, 58(9): Suppl S p. s539, Sep. 1, 2008.

Liao, et al., "Trail reduced joint inflammation, osteoclast activation and and loss in experimental arthritis", Allergy, 68(98):67 (2013).

Ma, et al., "TNF inhibitor therapy for rheumatoid arthritis (Review)", Biomed Reports, 1(2):177-84 (2012).

Akram, et al., "Alveolar epithelial cells in idiopathic pulmonary fibrosis display upregulation of TRAIL, DR4 and DR5 expression with simultaneous preferential over-expression of pro-apoptotic marker p53", Int. J. Clin. Exp. Pathol., 7(2): 552-564 (2014).

Azab, et al., "Elevated serum TRAIL levels in scloderma patients and its possible association with pulmonary involvement", Clinical Rheumatology; Journal of the International League of Associations for Rheumatology, 31(9):1359-1364 (2012).

Berendsen, "A glimpse of the holy grail", Science 282:642-3 (1998).

Bradley, et al., Limits of cooperativity in a structurally modular protein: Response of the notch ankyrin domain to analogous alanine substitutions in each repeat, J Mol Biol, 324:373-86 (2002).

Castellino, et al., The tumor necrosis factor-related apoptosis-inducing ligand-osteoprotegerin system in limited systemic sclerosis: a new disease marker? Rheumatology, 49(6):1173-1176 (2010).

Davidson, "Advances in therapy for type 2 GLP-1 receptor agonists and DPP-4 inhibitors", Cleveland Clinic J Med., 76: Supp 5 (2009).

Definition of Analogue and Derivative, On-line Medical Dictionary, accessed Mar. 5, 2000.

Gilbane, et al., "Scleroderma pathogenesis: a pivotal role for fibroblasts as effector cells", https://www/ncbi.nlm.nih.gov/pmc/articles/PMC4060542/pdf/ar4230.pdf retreived on Jul. 3, 2019.

Harith, et al., "On the TRAIL of obesity and diabetes", Trends Endocrinol. Metabol., 24(11):578-587 (2013).

Hasel, "In Chronic Pancreatitis, Widespread Emergence of TRAIL Receptors in Epithelia Coincides with Neoexpression of TRAIL by Pancreatic Stellate Cells of Early Fibrotic Areas", Laboratory Investigation, 83(6);825-836 (2003).

Inflammation & Immunity, 23:6, 517-521 (Oct. 2015).

Jiang, et al., "PEGylated TNF-related apoptosis-inducing ligand (TRAIL) for effective tumor combination therapy" Biomaterials, 32:8529-8537 (2011).

Kim, "The secretable form of trimeric TRAIL, a potent inducer of apoptosis", Biochem. Biophys. Res. Comm. 321:930-935 (2004).

Kinstler, et al., "Mono-N-terminal poly(ethylene glycol)-protein conjugates", Adv Drug Deliv., 54:477-85 (2002).

Lee, "A novel trail-based therapy for chronic pancreatitis", Gastroenterology, 152(55): S18 (2017).

Ngo, "Computational Complexity, Protein Structure Protection, and the Levinthal Paradox", The Protein Folding Problem and Tertiary Structure Prediction, 491-494 (1994).

Park, et al., "Targeting of dermal myofibroblasts through death receptor 5 arrests fibrosis in mouse models of scleroderma", Nature Communications, 10(1) (2019).

Park, et al., "Down-regulation of Fox0-dependent c-FLIP expression mediates Trail-induced apoptosis in activated hepatic stellate cells", Cell Signal., 21(10):1495-503 (2009).

Radaeva, et al., "Natural killer cells ameliorate liver fibrosis by killing activated stellate cells in NKG2D-dependent and tumor necrosis factor-related apoptosis-inducing ligand-dependent manners", Gastroenterology, 130(2):435-52 (2006).

Rudinger, "Peptide Hormones", JA Parsons, Ed pp. 1-7 (1976).

Sigma, "Design custom peptides", Sigma and Genosys, pp. 1-2 (2004).

Taimr, "Activated stellate cells express the TRAIL receptor-2/death receptor-5 and undergo TRAIL-mediated apoptosis", Hepatology, 37(1):89-95 (2003).

The definition of dimer, thefreedictionary.com, accessed on Dec. 8, 2014.

The definition of trimer, thefreedictionary.com, accessed on Dec. 8, 2014.

The Mayo Clinic, Diabetes, Diabetes Symptoms, www.mayoclinic.org/diseases-conditions/diabetes/in-depth/diabtes-symptoms/art, accessed on Dec. 9, 2014.

TNFSF10, symbol report, http://www.genenames.org/data/hgnc_data.php?hgnc_id=11925 , 1 page, downloaded Mar. 8, 2011.

Voet, "Abnormal hemoglobins", Biochemistry, (2):235-41 (1995).

Walczak, et al., "Tumoricidal activity of tumor necrosis factor-related apoptosis-inducing ligand in vivo", Nature Med., 5(2):157-63 (1999).

Wu, et al., "Regression of human mammary adenocarcinoma by systemic administration of a recombinant gene encoding the hFlex-TRAIL fusion protein", Molec. Therapy, 3(3): 368-374 (2001).

Xue, "Exedin 4-treatment of nonobese diabetic mice increases beta-cell proliferation and fractional insulin reactive area", Journal of Diabetes and Its Complications, 24:163-167 (2010).

Yoshioka, et al.,"Optimal site-specific PEGylation of mutant TNF-alpha improves its antitumor potency", Biochem Biophys Res Comm., 315:808-14 (2004).

Youn, et al., "Biological and physicochemical evaluation of the conformational stability of tumor nercrosis factor-related apoptosis-inducing ligand (TRAIL)", Biotechnol Lttrs., 29:713-21 (2007).

Bajaj, et al., "Conatumumab: a novel monoclonal antibody against death receptor 5 for the treatment of advanced malignancies in adults", Expert Opinion on Biological Therapy, 11(11):1519-1524 (2011).

(56) References Cited

OTHER PUBLICATIONS

Gong, et al., "Site-specific PEGylation of exenatide analogues markedly improved their glucoregulatory activity", Br J Pharmacol., 163(2):399-412 (2011).
Kim, "Mono-PEGylated dimeric exendin-4 as high receptor binding and long-acting conjugates for type 2 anti-diabetes therapeutics", Bioconjugate Chemistry, 22:625-632 (2011).
Klonowski-Stumpe, et al., "Apoptosis in activated rat pancreatic stellate cells", Am. J. Physiol. Gastorintest. Liver. Physiol., 283:G819-G826 (2002).
Pan, et al., Site-specific PEGylation of a muted-cysteine residue and its effect on tumor necrosis factor (TNF)-related apoptosis-inducing ligand (TRAIL), Biomaterials, 34:9115-9123 (2013).

* cited by examiner

LONG ACTING TRAIL RECEPTOR AGONISTS FOR TREATMENT OF AUTOIMMUNE DISEASES

CROSS REFERENCE TO RELATED APPLICATIONS

This application claims benefit of U.S. Provisional Application No. 61/951,393, filed Mar. 11, 2014, which is hereby incorporated herein by reference in its entirety.

REFERENCE TO SEQUENCE LISTING

The instant application contains a Sequence Listing which has been submitted in ASCII format via EFS-Web and is hereby incorporated by reference in its entirety. Said ASCII copy, created on Feb. 27, 2015, is named THER_102_ST25.txt and is 7,522 bytes in size.

FIELD OF THE INVENTION

The invention is generally directed to compositions and methods for treating autoimmune diseases, in particular long-lasting ligands and agonists of TRAIL receptor and method of their use for treating autoimmune diseases such as rheumatoid arthritis.

BACKGROUND OF THE INVENTION

Rheumatoid arthritis (RA) is a chronic inflammatory disorder that affects approximately 1% of the population. RA affects the synovial joints, typically in the small joints in hands and feet, causing painful swelling that leads to the irreversible destruction of cartilage and bone. It is characterized by the hyperplasia of synovium, which is initiated by the infiltration of immune cells (macrophages, T cells and B cells) in joints and the production of inflammatory cytokines like IL-1, TNF-alpha and IL-6 (McInnes, et al., Nature reviews Immunology, 7(6):429-42 (2007)). After initiation, fibroblast-like synoviocytes (FLS) maintain inflammation and joint destruction through loss of contact inhibition, activation of oncogenes and lack of apoptosis, similar properties to cancer cells. Hyperplasia directly leads to joint destruction with enhanced production of matrix-degrading enzymes. There is an upregulation of anti-apoptotic proteins like FLIP, Mcl-1 and xIAP in different cell populations within the area.

TRAIL is expressed by many cell types including activated T cells, natural killer cells and activated macrophages. It is a type-II membrane protein that binds to four membrane receptors, TRAIL-R1 (DR4), -R2 (DR5), -R3 (DcR1) and -R4 (DcR2), and one soluble receptor, OPG. DR4 and DR5 have a death domain, allowing them to trigger caspase-3 activation and apoptosis via recruitment of adaptor molecules and the formation of a Death Inducing Signaling Complex (DISC) when bound to TRAIL. Studies in mice, which only have one TRAIL receptor with a death domain, and human samples show that TRAIL plays a role in arthritis.

Song et al., first demonstrated that by blocking TRAIL with a recombinant soluble DR5 in a collagen-induced arthritis (CIA) mouse model, arthritis worsened due to hyperproliferation of synoviocytes and intra-articular lymphocytes coupled with increased production of cytokines and autoantibodies; but when TRAIL production was increased via intraarticular gene transfer through an adenoviral vector with mouse TRAIL genes, symptoms were diminished (Song K, et al., The Journal of Experimental Medicine, 191(7):1095-104 (2000)). Similarly, TRAIL production also decreased arthritis symptoms in IL-1β-induced arthritis in rabbits with human TRAIL genes (Yao, et al., Gene therapy, 10(12):1055-60 (2003)). The role of TRAIL in RA was also demonstrated using a mouse model deficient of TRAIL (TRAIL-/-).

Without TRAIL, the mice did not develop spontaneous autoimmune disease but did show a significant hypersensitivity to CIA (Lamhamedi-Cherradi, et al., Nature immunology 4(3):255-60 (2003)). Arthritis scores were nearly 8 times higher in TRAIL-/- mice than TRAIL+/+ mice 54 days after being immunized with chicken type collagen due to a significantly increased cellular and humoral immune response to collagen (Lamhamedi-Cherradi, et al., Nature immunology 4(3):255-60 (2003)). Based on cells grown from the synovial fluid and membrane of RA patients, fibroblasts were shown to specifically express functionally active DR5. Furthermore, these DR5 positive cells were susceptible to apoptosis when induced by a mouse monoclonal antibody (mAb) against human TRAIL-DR5 (Miranda-Carus, et al., Arthritis and rheumatism 50(9):2786-93 (2004)).

Other groups have also demonstrated that a daily injected anti-DR5 mAb can ameliorate arthritic symptoms in vivo by regulating the mRNA expression of DR5 and apoptosis-related genes along with prolonging the duration of the cell cycle (Li, et al., Experimental biology and medicine (Maywood, N.J.), 234(12):1468-76 (2009)). Another strategy for a TRAIL-based therapy uses dendritic cells transfected with an adenovirus to express inducible TRAIL in collagen II-induced arthritis-susceptible DBA/1j mice (Liu, et al., The Journal of clinical investigation, 112(9):1332-41 (2003)).

In summary, TRAIL and the DR4 and DR5 receptors have been identified in therapeutic strategies for treatment of RA (Anel A, et al., Frontiers in bioscience: a journal and virtual library, 12:2074-84 (2007)). However, although TRAIL has potent apoptotic activity on activated lymphocytes and anti-inflammatory activity, its rapid inactivation, low stability and solubility, fast renal clearance, and side-effects that include hepatotoxicity (Jo, et al., Nature medicine 6(5): 564-7 (2000)) after systemic delivery are obstacles to its clinical application. Reformulation of TRAIL to improve its biological half-life and bioactivity for RA treatment has been explored in animal models. Martinez-Lostao et al., conjugated bioactive TRAIL to artificial large unilamellar vesicles (LUVs) to resemble naturally secreted TRAIL as an RA treatment in a rabbit model of antigen-induced arthritis (AIA) (Martinez-Lostao, et al., Arthritis & Rheumatism, 62(8):2272-82 (2010)). LUVs bound TRAIL-His$_{10}$ via an Ni$^{2+}$-NTA-containing lipid: 1,2-dioleoyi-sn-glycero-3-{[N-(5-amino-1-carboxypentyl)-iminodiacetic acid]succinyl} (nickel salt) (DOGS-NTA). After being injected directly to the knee of the model, LUV-modified TRAIL showed a 62% improvement as a percentage of the maximal disease, while unmodified soluble TRAIL exhibited an improvement of 30% in the right knee. The improvement was marked by almost complete elimination of synovial Hyperplasia and decrease in inflammatory infiltrate and vascularity. The treatment lacked systemic toxicity and was not hepatotoxic (Martinez-Lostao, et al., Arthritis & Rheumatism, 62(8): 2272-82 (2010)). However, this system utilized direct injections to the site of RA, which is clinically undesirable because RA typically occurs at multiple joints and therefore causes pain and discomfort throughout the body of patients.

Previous studies also demonstrated that systemically, intraperitonealy, daily administered TRAIL significantly suppress the progression of RA in experimental animal models (Jin, et al., *The Journal of pharmacology and experimental therapeutics*, 332(3):858-65 (2010)). Although the study showed that systemically administered recombinant TRAIL could be used to treat RA, the approach required daily injections, which is also clinically undesirable. A subsequent study utilized a systemically injectable formulation of TRAIL complexed with hyaluronic acid, a naturally occurring biomaterial, to form a nanocomplex (Kim, et al., *Biomaterials*, 31(34):9057-64 (2010)). The formulation stabilized TRAIL for prolonged blood circulation during RA therapy. However, in this system, 5K-PEG-TRAIL alone at a low dose did not demonstrate positive efficacy when treated at one-week intervals, and stability and efficacy of TRAIL was dependent on hyaluronic acid.

Accordingly, there remains a need for improved TRAIL-based formulations for treatment of autoimmune diseases, particularly rheumatoid arthritis.

Therefore, it is an object of the invention to provide TRAIL-based formulations and dosage regimens thereof for treatment of autoimmune diseases, particularly rheumatoid arthritis.

It is another object of the invention to provide TRAIL-based combination therapies for and dosage regimens thereof for treatment of autoimmune diseases, particularly rheumatoid arthritis.

SUMMARY OF THE INVENTION

Methods of treating an autoimmune disease such as rheumatoid arthritis, methods of increasing apoptosis of pro-inflammatory immune cells or synoviocytes, methods of increasing the quantity of the anti-inflammatory regulatory T cells (Treg), and methods of slowing the progression of inflammation in a subject are provided. The methods typically include systemically administering a pharmaceutical composition including an effective amount of TRAIL-conjugate. The pharmaceutical composition is formulated for administration no more than twice weekly, and preferably no more than once weekly. In preferred embodiments, the TRAIL-conjugate is effective in alleviating the autoimmune disorder for at least three days, preferably at least seven days, optionally, at least 10 day.

The TRAIL-conjugate typically includes a TRAIL polypeptide including a fragment of human TRAIL effective to bind to and induce apoptotic signaling through TRAIL-R1 or TRAIL-R2 linked to polyethylene glycol or a derivative thereof. In particular embodiments the TRAIL polypeptide is a fusion protein including a trimerization domain. For example, in a specific embodiment, the TRAIL conjugate includes an isoleucine zipper domain including amino acids 114-281 of SEQ ID NO:1 conjugated to 5 kilodalton polyethylene glycol. The dosage of the TRAIL-conjugate is typically 0.01-1,000 mg/kg, 1-100 mg/kg, 5-50 mg/kg, or 10-20 mg/kg; or 1-1,000 mg/m², 10-100 mg/m², 25-75 mg/m², or 40-60 mg/m². The conjugate does not include other proteins such as hyaluronic acid or being part of a nanocomplex that modulates the circulation half-life or release kinetics of the TRAIL-conjugate.

In preferred embodiments, the methods can reduce, or prevent an increase, in joint swelling, erythema, joint rigidity, inflammatory cell infiltration into the joint(s), synovitis, pannus formation, destruction of articular cartilage, bone erosion, elevated erythrocyte sedimentation rates (ESR), or anaemia; reduce, or prevent an increase, in expression or circulating levels of one or more inflammatory molecules such as ICAM-1, COX-2, iNOS and pro-inflammatory molecules such as TNF-α, IL-1β, IFN-γ, IL-2, IL-6, and IL-17; increase in expression or circulating levels of anti-inflammatory molecules such as TGF-β, IL-10; reduce, or prevent an increase, in expression or circulating levels of autoantibodies; or combinations thereof. The symptom(s) to be alleviated will be characteristic of the disease to be treated. Exemplary autoimmune diseases include rheumatoid arthritis, scleroderma, Crohn's disease, psoriasis and lupus.

Combination therapies include administering a second active agent. In preferred embodiments, the second active agent is an agent used to treat rheumatoid arthritis, and most preferably a type of DMARD (disease modifying antirheumatic drugs) or a TNF-α inhibitor. Exemplary DMARDs include, but are not limited to, methotrexate, sulfasalazine, hydroxychloroquine and leflunomide. Exemplary TNF-α inhibitors include, but are not limited to, etanercept, infliximab, adalimumab, golimumab, and certolizumab pegol. In preferred embodiments, the effect of the combination is greater than the additive effect of the two agents administered as monotherapies. The TRAIL-conjugate and the second active agent can be co-administered as part of the same pharmaceutical composition or co-administered in different pharmaceutical compositions. The TRAIL-conjugate and the second active agent can be administered separately but simultaneously, or sequentially.

Pharmaceutical composition dosage units including a TRAIL-conjugate and a TNF-α inhibitor in an effective amount for a single once weekly dose for treatment of rheumatoid arthritis are also provided.

DETAILED DESCRIPTION OF THE INVENTION

I. Definitions

Figure 1A:
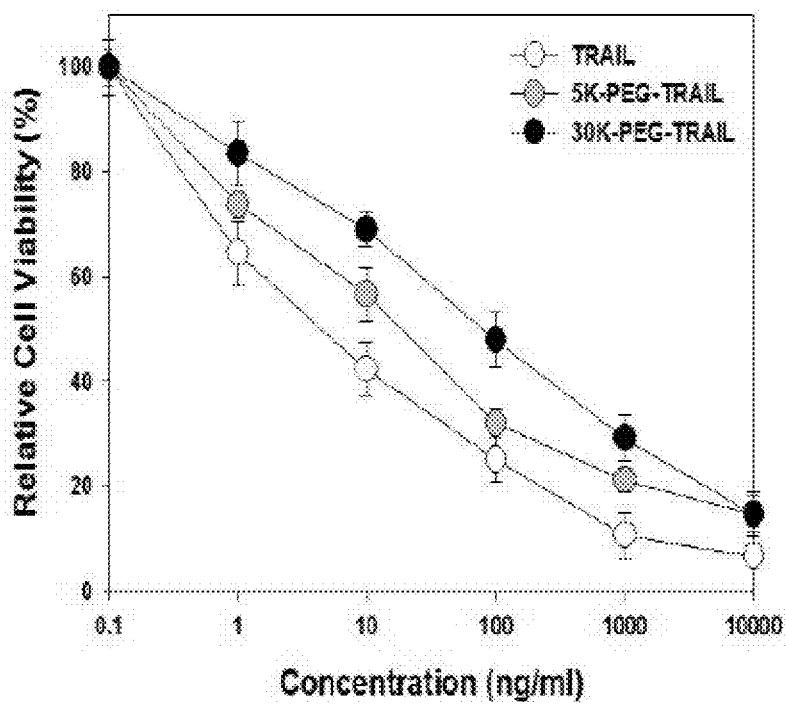
FIG. 1A is a line graph showing the apoptotic effect (Relative Cell Viability (%)) of increasing concentration (ng/ml) of TRAIL and PEG-TRAIL analogs (5K-, 30K-PEG-TRAIL) on Jurkat cells.

As used herein, an "immune cell" refers to any cell from the hemopoietic origin including but not limited to T cells, B cells, monocytes, dendritic cells, and macrophages.

As used herein, the terms "individual", "host", "subject", and "patient" are used interchangeably, and refer to a mammal, including, but not limited to, primates, for example, human beings, as well as rodents, such as mice and rats, and other laboratory animals.

As used herein, the term "treating" includes inhibiting, alleviating, preventing or eliminating one or more symptoms or side effects associated with the disease, condition, or disorder being treated.

The term "reduce", "inhibit", "alleviate" or "decrease" are used relative to a control. One of skill in the art would readily identify the appropriate control to use for each experiment. For example a decreased response in a subject or cell treated with a compound is compared to a response in subject or cell that is not treated with the compound.

As used herein the term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease, and the treatment being administered. The effect of the effective amount can be relative to a control. Such controls are known in the art and discussed herein, and can be, for example the condition of the subject prior to or in the absence of administration of the drug, or drug combination, or in the case of drug combinations, the effect of the combination can be compared to the effect of administration of only one of the drugs.

As used herein, the term "combination therapy" refers to treatment of a disease or symptom thereof, or a method for achieving a desired physiological change, including administering an effective amount of two or more chemical agents or components to treat the disease or symptom thereof, or to produce the physiological change, wherein the chemical agents or components are administered together, such as part of the same composition, or administered separately and independently at the same time or at different times (i.e., administration of each agent or component is separated by a finite period of time from each other).

As used herein, the term "dosage regime" refers to drug administration regarding formulation, route of administration, drug dose, dosing interval and treatment duration.

As used herein, the term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains the same mechanism of activity. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptide as determined by the match between strings of such sequences. "Identity" can also mean the degree of sequence relatedness of a polypeptide compared to the full-length of a reference polypeptide. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M, and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

II. TRAIL-Conjugates

It has been discovered that the ligands and agonists of agonistic TRAIL receptors can be formulated such that the ligand is effective for treating an autoimmune disease when administered as a single dose less frequently than daily, such as twice weekly, more preferably once weekly, or even more preferably less than once weekly. The formulations are advantageous because they do not require local injection at the site of inflammation, and can instead be administered.

In preferred embodiments, the ligand or agonist does not require a delivery vehicle such as a controlled or sustained release formulation to be effective.

The ligands and agonists disclosed herein are typically TRAIL conjugates that include a TRAIL peptide, or mimic, preferably TRAIL or a fragment, variant, or fusion thereof, linked to a conjugate molecule that extends the in vivo half-life of the TRAIL-conjugate when compared to the TRAIL fragment, variant, or fusion in the absence of the conjugate molecule.

As discussed in more detail below, and shown in the working Example, it has been discovered that the disclosed TRAIL-conjugate formulations and dosage regimes can reduce humoral and cellular immune responses that contribute to autoimmune disease. For example, systemic PEG-TRAIL administrations strongly reduced and/or normalized the inflammatory response during arthritis development by down-regulating inflammatory molecules including ICAM-1, COX-2, iNOS and pro-inflammatory cytokine levels including TNF-α, IL-1β, INF-γ, IL-2, IL-6, and IL-17. In addition, PEG-TRAIL treatment increased the quantity of the anti-inflammatory Foxp3$^+$ regulatory T (Treg) cells. The compounds also reduced humoral immunity as evidenced by a reduction in circulating auto antibodies, including both IgG2a and IgG1 that initiate joint inflammation. As discussed in more detail below, the disclosed compositions are typically administered to a subject in need thereof in amount effective to 1) reduce a cellular immune response or a biomarker associated therewith, such as circulating levels of one or more inflammatory molecules and pro-inflammatory cytokines; 2) reduce a humoral response or biomarker associated therewith, such as circulating levels of pathological autoantibodies; 3) increase the quantity of the Treg cells; or 4) a combination thereof.

A. TRAIL Peptides and Analogues

TRAIL-conjugates include a TRAIL domain, which is typically a TRAIL peptide, analogue, or mimic, preferably TRAIL or a fragment, variant, or fusion thereof to which a conjugate molecule is linked.

1. TRAIL

TRAIL/Apo2L (TNFSF10) was originally identified in searches of EST databases for genes with homology to known TNF superfamily ligands (Benedict et al., *J. Exp. Med.,* 209(11):1903-1906 (2012)). In humans, TRAIL binds two proapoptotic death receptors (DRs), TRAIL-R1 and -R2 (TNFRSF10A and 10B), as well as two other membrane receptors that do not induce death and instead may act as decoys for death signaling. TRAIL binding to its cognate DRs induces formation of a death-inducing signaling complex, ultimately leading to caspase activation and initiation of apoptosis (Benedict et al., *J. Exp. Med.,* 209(11):1903-1906 (2012)).

In some embodiments, the TRAIL conjugate includes a TRAIL peptide, or an agonistic TRAIL receptor binding fragment or variant thereof.

Nucleic acid and amino acid sequence for human TRAIL are known in the art. For example, an amino acid sequence for human TRAIL is MAMMEVQGGPSLGQTCVLIVIFTVLLQSLCVAVTYVYFTNELKQMQDKYSKSGIACFLKE DDSYWDPNDEESMNSPCWQVKWQLRQLVRKMILRTSEETISTVQEKQQNISPLVRERGPQ RVAAHITGTRGRSNTLSSPNSKNEKALGRKINSWESSRSGHSFLSNLHLRNGELVIHEKG FYYIYSQTYFRFQEEIKENTKNDKQMVQYIYKYTSYPDPILLMKSARNSCWSKDAEYGLY SIYQGGIFELKENDRIFVSVTNEHLIDMDHEASFFGAFLVG (SEQ ID NO:1, (UniProtKB database accession no. P50591 (TNF10_HUMAN)). In some embodiments, the TRAIL conjugate includes a TRAIL peptide including or having the amino acid sequence of SEQ ID NO:1.

Preferably, the TRAIL is a soluble TRAIL. Endogenous, full-length TRAIL includes a cytoplasmic domain, a transmembrane domain, and an extracellular domain. Typically, soluble TRAIL is a fragment of full-length TRAIL without the cytoplasmic domain and the transmembrane domain. Therefore, soluble TRAIL can be the extracellular domain of TRAIL (e.g., extracellular domain of SEQ ID NO:1), or a functional fragment thereof. A consensus extracellular domain for the TRAIL of SEQ ID NO:1 is amino acids 39-281 of SEQ ID NO:1. Therefore, in some embodiments, the TRAIL conjugate includes a TRAIL peptide including or having amino acids 39-281 of SEQ ID NO:1, or a functional fragment or variant thereof.

In some embodiments, the TRAIL conjugate includes a functional fragment or variant of SEQ ID NO:1 that can agonize signaling through TRAIL-R1 and/or TRAIL-R2. The fragment or variant of SEQ ID NO:1 can have 50, 60, 70, 75, 80, 85, 90, 95, 96, 97, 98, 99, or more than 99% sequence identity to SEQ ID NO:1.

Preferably, the functional fragment or variant thereof includes the extracellular domain of SEQ ID NO:1, or a functional fragment thereof. It is believed that the C-terminal 150 amino acid of TRAIL includes the receptor binding domain. Therefore, in some embodiments, the functional fragment includes amino acids 132-281 of SEQ ID NO:1. In other particular embodiments, the fragment is amino acids 95-281, or amino acids 114-281 of SEQ ID NO:1.

Variants can have one or more substitutions, deletions, or additions, or any combination thereof relative to SEQ ID NO:1. In some embodiments, the variant is a naturally occurring alternative sequence, splice variant, or substitution, addition or deletion variant, or the extracellular domain is a functional fragment of an alternative sequence, splice variant, or substitution, addition or deletion variant. Naturally occurring alternative sequences and variants are disclosed in UniProtKB database accession no. P50591 (TNF10_HUMAN), version 140 (last modified Jan. 22, 2014.

All of the Trail proteins described herein can be made using standard techniques for isolation of natural or recombinant proteins, and chemical modified as described herein.

2. TRAIL Analogues

TRAIL can interact with its receptors as a trimer. Therefore, in some embodiments, the ligand or agonist used in the methods disclosed herein is, or can form, a multimer, preferably a trimer. The trimer can be a homotrimer, or a heterotrimer.

The TRAIL conjugate can include a TRAIL analogue, or an agonistic TRAIL receptor binding fragment or variant thereof. TRAIL analogues are known in the art. In preferred embodiments, the analogues have increased affinity or specificity for one or more agonistic TRAIL receptors (e.g., TRAIL-R1 (DR4) and/or TRAIL-R2 (DR5)), reduced affinity or specificity for one or more antagonistic or decoy TRAIL receptors (e.g., receptors DcR1 and DcR2) or a combination thereof compared to wildtype or endogenous TRAIL.

In some embodiments, the analogue is a DR4-selective mutant of wildtype TRAIL. DR-4 selective mutants are known in the art and disclosed in, for example, Tur, *The Journal of Biological Chemistry,* 283(29):20560-8 (2008). In a particular embodiments, the analogue is a variant of SEQ ID NO:1 having a D218H or a D218Y substitution, or a functional fragment thereof (e.g., the extracellular domain).

In some embodiments, the analogue is a DR5-selective mutant of wildtype TRAIL. Particular DR-5-selective mutants include variants of SEQ ID NO:1 having D269H, D269H/E195R, or D269H/T214R, and functional fragments thereof (e.g., the extracellular domain). Such variants are described in van der Sloot, *Proceedings of the National Academy of Sciences of the United States of America,* 103(23):8634-9 (2006).

3. TRAIL Fusion Proteins

The TRAIL conjugate can be a TRAIL fusion protein. TRAIL fusion polypeptides have a first fusion partner including all or a part of a TRAIL protein extracellular domain fused (i) directly to a second polypeptide or, (ii) optionally, fused to a linker peptide sequence that is fused to the second polypeptide. The fusion proteins optionally contain a domain that functions to dimerize or multimerize two or more fusion proteins. The peptide/polypeptide linker domain can either be a separate domain, or alternatively can be contained within one of the other domains (TRAIL polypeptide or second polypeptide) of the fusion protein. Similarly, the domain that functions to dimerize or multimerize the fusion proteins can either be a separate domain, or alternatively can be contained within one of the other domains (TRAIL polypeptide, second polypeptide or peptide/polypeptide linker domain) of the fusion protein. In one embodiment, the dimerization/multimerization domain and the peptide/polypeptide linker domain are the same.

Fusion proteins disclosed herein can be of formula I:

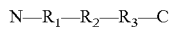

wherein "N" represents the N-terminus of the fusion protein, "C" represents the C-terminus of the fusion protein, "$R_1$" is a TRAIL polypeptide, "$R_2$" is an optional peptide/polypeptide linker domain, and "$R_3$" is a second polypeptide. Alternatively, $R_3$ may be the TRAIL polypeptide and $R_1$ may be the second polypeptide.

The fusion proteins can be dimerized or multimerized. Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric.

The presence of the second polypeptide can alter the solubility, stability, affinity and/or valency of the TRAIL fusion polypeptide. As used herein, "valency" refers to the number of binding sites available per molecule. In some embodiments, the second polypeptide contains one or more domains of an immunoglobulin heavy chain constant region, preferably having an amino acid sequence corresponding to the hinge, $C_H2$ and $C_H3$ regions of a human immunoglobulin Cγ1 chain or to the hinge, $C_H2$ and $C_H3$ regions of a murine immunoglobulin Cγ2a chain. In a particular dimeric fusion protein, the dimer results from the covalent bonding of Cys residue in the hinge region of two of the Ig heavy chains that are the same Cys residues that are disulfide linked in dimerized normal Ig heavy chains.

In a particular embodiment, the TRAIL fusion protein is a TRAIL-mimic including three TRAIL-protomer subsequences combined in one polypeptide chain, termed the single-chain TRAIL-receptor-binding domain (scTRAIL-RBD), as described in Gieffers, *Molecular Cancer Therapeutics*, 12(12):2735-47 (2013). Two of the so-called scTRAIL-RBDs, with three receptor binding sites each, can be brought in close proximity resulting in a multimeric fusion protein with a hexavalent binding mode. In some embodiments, multimerization is achieved by fusing the Fc-part of a human immunoglobulin G1 (IgG1)-mutein C-terminally to the scTRAIL-RBD polypeptide, thereby creating six receptor binding sites per drug molecule.

Forcing dimerization of scFv-scTRAIL based on scFv linker modification for a targeted scTRAIL composed predominantly of dimers (Db-scTRAIL) exceed the activity of nontargeted scTRAIL approximately 100-fold for some target cell types (Siegemund, supra). Increased activity of Db-scTRAIL was also demonstrated on target-negative cells, indicating that, in addition to targeting, oligomerization equivalent to an at least dimeric assembly of standard TRAIL per se enhances apoptosis signaling. Therefore, in preferred embodiments, the TRAIL fusion proteins have a multimerization domain, such as a dimerization or trimerization domain, or a combination thereof that can lead to, for example, dimeric, trimeric, or hexameric molecule.

Another fusion protein that facilitates trimer formation includes a receptor binding fragment of TRAIL amino-terminally fused to a trimerizing leucine or isoleucine zipper domain.

TRAIL fusion proteins and results of using the fusion proteins in functional assays are also described in, Wahl, *Hepatology*, 57(2):625-36 (2013).

B. Conjugates and Complexes

The disclosed TRAIL-conjugates also include a second conjugate molecule that is linked to the TRAIL domain.

1. Polyalkylene Oxides such as PEG

Studies show that the pharmacokinetic and pharmacodynamic profiles of TRAIL can be improved using PEGylation (Kim, et al., *Bioconjugate Chem.*, 22 (8), pp 1631-1637 (2011)). Studies show that TRAIL analogues derivatized with PEG maintain anti-cancer activity, while also exhibiting higher metabolic stabilities in plasma, extended pharmacokinetic profiles, and greater circulating half-lives (Chae, et al., *Molecular cancer therapeutics* 9(6):1719-29 (2010); Kim, et al., *Bioconjugate chemistry*, 22(8):1631-7 (2011); Kim, et al., *Journal of pharmaceutical sciences* 100(2):482-91 (2011); Kim, et al., *Journal of controlled release: official journal of the Controlled Release Society* 150(1):63-9 (2011)).

Therefore, in some embodiments, the TRAIL domain is derivatized with one or more ethylene glycol (EG) units, more preferably 2 or more EG units (i.e., polyethylene glycol (PEG)), or a derivative thereof. Derivatives of PEG include, but are not limited to, methoxypolyethylene glycol succinimidyl propionate, methoxypolyethylene glycol N-hydroxysuccinimide, methoxypolyethylene glycol aldehyde, methoxypolyethylene glycol maleimide and multiple-branched polyethylene glycol.

The precise number of EG or derivative units depends on the desired activity, plasma stability, and pharmacokinetic profile. For example, Kim, et al. (supra) reported that 2, 5, 10, 20, and 30K-PEG-TRAIL resulted in greater circulating half-lives of 3.9, 5.3, 6.2, 12.3, and 17.7 h respectively in mice, versus 1.1 h for TRAIL. In some embodiments, the molecular weight of the PEG is between about 1 and 100 kDa, preferably between about 1 and 50 kDa.

For example, the PEG can have a molecular weight of "N" kDa, wherein N is any integer between 1 and 100. The PEG can have a molecular weight of "N" Da, wherein N is any integer between 1,000 and 1,000,000. In a particular embodiment, the molecular weight of the PEG is "N" Da, wherein "N" is between 1,000 and 60,000, or more preferably between 5,000 and 40,000.

The pro-apoptotic agent can be conjugated with linear or branched PEG. Some studies have shown that proteins derivatized with branched PEG have extended in vivo circulation half-lives compared to linear PEG-proteins, thought to be due partly to a greater hydrodynamic volume of branched PEG-proteins (Fee, et al., *Biotechnol Bioeng.*, 98(4):725-3 (2007)).

Peptide ligands can be derivatized at the C-terminus, or preferably at the N-terminus, using methods that are known in the art.

The TRAIL-PEG conjugates may be depicted by the following formula:

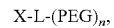

wherein

X represents a TRAIL protein,

L represents a linker,

PEG represents a branched poly(ethylene glycol) chain, and n is an integer selected from 2, 3, 4, 5, 6, 7 or 8.

In certain embodiments, n is 2.

The polyalkylene oxide is coupled to the protein via a linker. The linker may be a polyalkylene oxide, and preferably connects two polyalkylene oxide polymers to the protein.

In a particular embodiment, the TRAIL-conjugate is a PEG-conjugate that includes a TRAIL domain including a truncated form of human TRAIL, for example, from arginine-114 to glycine-281 of the full-length form (1-281) of human TRAIL, and PEG having a molecular weight between 1,000 and 100,000 Daltons, and preferably between 5,000 and 50,000 Daltons.

N-terminal modified PEG-TRAIL conjugates can be obtained by reacting an N-terminal amine of the TRAIL domain with an aldehyde group of the PEG in the presence of a reducing agent. PEG and TRAIL can be reacted at a molar ratio (PEG/TRAIL) of 2 to 10, or preferably 5 to 7.5.

In preferred embodiments, the TRAIL-conjugate includes a zipper amino acid motif, for example, an isoleucine zipper motif, that allows for trimer formation between three TRAIL-conjugate monomers.

The PEG chains are preferably, but not necessarily, of equal molecular weight. Exemplary molecular weight ranges for each PEG chain is between about 10 kDa and 60 kDa, and preferably about 20 kDa and 40 kDa. PEG40 is a branched PEG moiety was synthesized and has a molecular weight of 40 kDa: 20+20 kDa (each PEG chain).

A trimeric PEG moiety can consist of a branched PEG chain attached to a linker arm. A visual description of the trimer PEG moiety is provided immediately below.

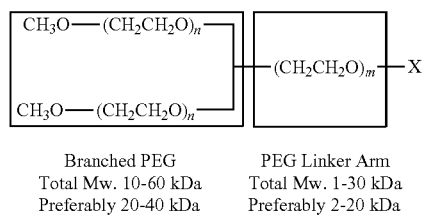

Branched PEG
Total Mw. 10-60 kDa
Preferably 20-40 kDa

PEG Linker Arm
Total Mw. 1-30 kDa
Preferably 2-20 kDa

The following trimeric PEGs were synthesized: YPEG42, YPEG43.5, YPEG45, YPEG50 and YPEG60.
  YPEG42 is a trimeric PEG moiety which has a molecular weight of 42 kDa: (20+20 kDa) (branched PEG)+2 kDa (linker arm).
  YPEG43.5 is a trimeric PEG moiety which has a molecular weight of 43.5 kDa: (20+20 kDa) (branched PEG)+3.5 kDa (linker arm).
  YPEG45 is a trimeric PEG moiety which has a molecular weight of 45 kDa: (20+20 kDa) (branched PEG)+5 kDa (linker arm).
  YPEG50 is a trimeric PEG moiety which has a molecular weight of 50 kDa: (20+20 kDa) (branched PEG)+10 kDa (linker arm).
  YPEG60 is a trimeric PEG moiety which has a molecular weight of 60 kDa: (20+20 kDa) (branched PEG)+20 kDa (linker arm).

2. Linker Moiety

The protein or peptide is covalently joined to the branched PEG moiety via a linker. The linker is a polymer, and generally has an atomic length of at least 800 angstroms. Typically, the linker has an atomic length from about 800 to about 2,000 angstrom, from about 800 to about 1,500 angstrom, from about 800 to about 1,000 angstrom, or from about 900 to about 1,000 angstrom. It is to be appreciated that the atomic distances listed above refer to fully extended polymers, and that when in the solid state or solution the linker may fold or curl in ways such that the actual distance between the branched PEG and protein or peptide is less than the atomic lengths listed above.

In certain embodiments, the linker is a poly(ethylene glycol) derivative with a molecular weight between about 1 kDa to 30 kDa, preferably from about 2 kDa to 20 kDa. A linker may also be a natural or unnatural amino acid of at least 80 units in length.

PEG alternatives for the linker include synthetic or natural water-soluble biocompatible polymers such as polyethylene oxide, polyvinyl alcohol, polyacrylamide, proteins such as hyaluronic acid and chondroitin sulfate. celluloses such as hydroxymethyl cellulose, polyvinyl alcohol, and polyhydroxyalkyl (meth)acrylates.

Proteins and peptides may be covalently bound to the linker using conventional chemistries. Primary amine groups, such as found at the N-terminus or in lysine residues, will react with aldehydes and their equivalents under reductive conditions to give amines. (Molineux, Current pharmaceutical design, 10(11):1235-1244 (2004)). Mercapto (—SH) groups, such as found in cysteine residues, can undergo a conjugate addition with a variety of Michael acceptors, including acrylic and methacrylic acid derivatives, as well as maleimides (Gong et al., *British Journal of Pharmacology*, 163(2):399-412 (2011)). Other suitable nucleophilic groups found in peptides and proteins include disulfide bonds (Brocchini, et al., *Nature protocols*, 1:2241-2252 (2006)) and histidine residues (Cong, et al., *Bioconjugate Chemistry*, 23(2):248-263 (2012)).

The linker may be covalently joined to the protein or peptide using conventional chemistries. For instance, the linker polymer may be derivatized at one end with an electrophilic group such as an aldehyde, epoxide, halogen (chlorine, bromide, iodine), sulfonate ester (tosylate, mesylate), Michael acceptor, or activated carboxylates and then reacted with a nucleophilic amine or thiol group in the protein or peptide. Suitable Michael acceptors include acrylic and methacrylic acid derivatives such as acrylamides, methacrylamides, acrylates and methacrylates, as well as maleimides. Suitable activated carboxylates include nitrophenyl carbonate and NHS (N-hydroxy succinate) esters. In other embodiments, peptides and proteins containing arginine residues may be covalently joined with a linker containing a reactive 1,3 diketone functional group.

The conjugates may be prepared by first joining the linker with the peptide or protein, followed by joining the linker with the branched poly(ethylene glycol), or by first joining the linker with the branched poly(ethylene glycol), followed by joining the linker with the peptide or protein. The optimal sequence of bond formation is determined by the specific chemical transformations involved.

2. Macromolecules

In other embodiments, TRAIL can be derivatized as a long-acting TRAIL with an extended half-life using biopolymers or polypeptides through reported methods; for example, but not limited to, using chemically conjugated hyaluronic acid (Yang et al., *Biomaterials* 32(33); 8722-8729 (2011), depot forming polypeptides (Amiram et al., *Proc natl Acad Sci USA*, 110(8); 2792-2792 (2013), U.S. Published application Ser. No. 13/795,992) and TRAIL linked to extended recombinant polypeptides (U.S. Published application Ser. No. 12/699,761).

3. Complexes

The TRAIL domain can be complexed with a negatively charged moiety. In some embodiments the negatively charged moiety can facilitate loading of the ligand or agonist into a nanoparticle for extended, sustained, or time released delivery. In some embodiments, the negatively charged moiety itself mediates extended, sustained, or time released delivery of the ligand or agonist. Preferably, the negatively charged moiety does not substantially reduce the ability of the ligand or agonist to induce or enhance apoptosis in immune cells or synoviocytes.

The formation of a complex between positively charged TRAIL and the negatively charged chondroitin sulfate (CS) (CS/TRAIL) was developed and shown to facilitate loading of TRAIL in poly(lactide-co-glycolide) (PLGA) microspheres (MSs), without compromising the activity of the TRAIL (Kim, et al., *Journal of Pharmacy and Pharmacology*, 65(1):11-21 (2013). A nanocomplex of approximately 200 nm was formed in a weight ratio of 2 TRAIL to CS (TC2) at pH 5.0. The complex had >95% higher loading efficiency in PLGA MSs prepared by the multi-emulsion method than that of native TRAIL. Therefore, in some embodiments, the ligand or agonist, particularly TRAIL peptides, and variants, functional fragments and fusion proteins thereof, or conjugates thereof such as PEG-conjugates are complexed with chondroitin sulfate and optionally loaded into micro- or nanoparticles, for example, PLGA-based particles.

In other embodiments, the ligand or agonist, particularly TRAIL peptides, and variants, functional fragments and fusion proteins thereof, or conjugates thereof such as PEG-conjugates are complexed with hyaluronic acid (HA). Nanocomplexes of PEG-TRAIL and HA prepared by mixing positively charged PEG-TRAIL and negatively charged HA, were shown to have sustained delivery in vivo, with negligible loss of bioactivity compared with the PEG-TRAIL (Kim, et al., *Biomaterials,* 31(34):9057-64 (2010)). Delivery was further enhanced by administering the nanoparticles in a 1% HA containing solution. In an alternative embodiment, the HA is conjugated to the ligand or agonist as in Yang, et al., *Biomaterials,* 32(33):8722-9 (2011). Yang describes a coupling reaction between an aldehyde modified HA and the N-terminal group of IFNα, which can be used to couple HA to the pro-apoptotic agents disclosed herein. The IFNαcontent could be controlled in the range of 2-9 molecules per single HA chain with a bioconjugation efficiency higher than 95%, and the conjugates exhibited improved activity and half-life in vivo.

In some embodiments, the pro-apoptotic agent is modified to improve purification, Tag-removal, facilitate small molecule attachment or a combination thereof. Applied in tandem, elastin-like polypeptides and the Sortase A (SrtA) transpeptidase provide a method for chromatography-free purification of recombinant proteins and optional, site-specific conjugation of the protein to a small molecule (Bellucci, et al., *Angewandte Chemie International Edition,* 52(13):3703-3708 (2013)). This system provides an efficient mechanism for generating bioactive proteins at high yields and purities.

Other tags and labels are known in the art and include, for example, SUMO tags, His tags which typically include six or more, typically consecutive, histidine residues; FLAG tags, which typically include the sequence DYKDDDDK (SEQ ID NO:2); haemagglutinin (HA) for example, YPYDVP (SEQ ID NO:3); MYC tag for example ILK-KATAYIL (SEQ ID NO:4) or EQKLISEEDL (SEQ ID NO:5). Methods of using purification tags to facilitate protein purification are known in the art and include, for example, a chromatography step wherein the tag reversibly binds to a chromatography resin.

Purification tags can be at the N-terminus or C-terminus of the fusion protein. The purification tags can be separated from the polypeptide of interest in vivo (e.g., during expression), or ex vivo after isolation of protein. Therefore, purification tags can also be used to remove the fusion protein from a cellular lysate following expression. The fusion protein can also include an expression or solubility enhancing amino acid sequence. Exemplary expression or solubility enhancing amino acid sequences include maltose-binding protein (MBP), glutathione S-transferase (GST), thioredoxin (TRX), NUS A, ubiquitin (Ub), and a small ubiquitin-related modifier (SUMO).

4. Targeting Moieties

The TRAIL-conjugate, compositions including the TRAIL-conjugate agent, and delivery vehicles for the TRAIL-conjugate agent can include a targeting moiety. In some embodiments, the targeting moiety increases targeting to or accumulation of the pro-apoptotic agent to the organ of interest or target cells.

In a preferred embodiment, the targeting moiety increases targeting to or accumulation of the pro-apoptotic agent in the joints of subjects with rheumatoid arthritis, and/or to pro-inflammatory immune cells, synoviocytes, or a combination thereof. In other embodiments, the targeting moiety increases targeting to or accumulation of the agent in areas of inflammation or areas in which inflammatory cells are produced.

In some embodiments, the targeting molecules are fused with or conjugated to the TRAIL-conjugate itself, or to a composition that includes the TRAIL-conjugate, or delivery vehicles carrying the TRAIL conjugate (e.g., a carrier such as a micro- or nanoparticle, liposome, etc).

The molecule can target a protein expressed in the joint, or preferably on the surface of or in the microenvironment around pro-inflammatory immune cells, particularly those causing or contributing to joint inflammation or other symptoms of autoimmune disease, particular rheumatoid arthritis. The molecule can target a protein expressed in the synovium, or preferably on the surface of in the microenvironment around synoviocytes. The targeting moiety can be, for example, an antibody or antibody fragment such as immunoglobulin (antibody) single variable domains (dAbs) that binds to an antigen expressed in the liver, or more preferably on the surface of liver cells or in the microenvironment around hepatic stellate cells. In certain embodiments, the antibody is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art. In preferred embodiments, the targeting antibody or fragment thereof is specific for pro-inflammatory immune cell surface marker or synoviocyte surface marker, and is produced to reduce potential immunogenicity to a human host as is known in the art. For example, transgenic mice which contain the entire human immunoglobulin gene cluster are capable of producing "human" antibodies can be utilized. In one embodiment, fragments of such human antibodies are employed as targeting signals. In a preferred embodiment, single chain antibodies modeled on human antibodies are prepared in prokaryotic culture.

C. Formulations

Formulations of and pharmaceutical compositions including one or more active agents are provided. The pharmaceutical compositions can include one or more additional active agents. Therefore, in some embodiments, the pharmaceutical composition includes two, three, or more active agents. The pharmaceutical compositions can be formulated as a pharmaceutical dosage unit, also referred to as a unit dosage form. Such formulations typically include an effective amount a TRAIL-conjugate. Effective amounts of the disclosed TRAIL-conjugates are discussed in more detail below.

Pharmaceutical compositions can be for administration by parenteral (intramuscular, intraperitoneal, intravenous (IV) or subcutaneous injection), or nasal or pulmonary administration and can be formulated in dosage forms appropriate for each route of administration.

Preferably, the compositions are administered locally, for example by injection directly into a site to be treated (e.g., into a joint). In some embodiments, the compositions are injected or otherwise administered directly into the vasculature at or adjacent to the intended site of treatment (e.g., adjacent to the joint). Typically, local administration causes an increased localized concentration of the compositions which is greater than that which can be achieved by systemic administration.

The formulations are preferably an aqueous solution, a suspension or emulsion. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

III. Methods of Use

The conjugated TRAIL proteins have extended half-lives relative to their unconjugated counterparts due to their increased molecular size. Because the linker permits the protein or peptide to more easily interact with its biological target, the biological potency of the conjugate is not substantially reduced, as is typically observed with PEGylated proteins and peptides. Since the half-life is extended without concurrent loss of potency, the conjugates may be administered at lower dosage levels and dosing frequencies compared to the unconjugated protein or peptide, or compared to proteins and peptides conjugated according to protocols disclosed in the prior art.

The Examples below show that 5K-PEG-TRAIL (i.e., a PEG-TRAIL conjugate with a 5,000 Dalton PEG) is effective for treatment for rheumatoid arthritis when administered every three days, while a 30K-PEG-TRAIL (i.e., a PEG-TRAIL conjugate with a 30,000 Dalton PEG) is effective when administered once weekly. Therefore, in some embodiments, a large molecular weight PEG conjugate is associated with a longer in vivo half-life.

A. Disease or Disorders to be Treated

The TRAIL compositions are useful for treatment of autoimmune disease or inflammatory disease or disorder. Representative inflammatory or autoimmune diseases/disorders that can be treated using the disclosed compositions include, but are not limited to, rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, *pemphigus vulgaris*, pernicious anemia, polyarteritis *nodosa*, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

In a preferred embodiment, the inflammatory and autoimmune disease/disorder is rheumatoid arthritis.

B. Methods of Treatment

Methods of treating autoimmune diseases, particular rheumatoid arthritis are provided. The methods typically include administering to a subject in need thereof an effective amount of a TRAIL-conjugate. Typically, the TRAIL-conjugate is administered in an effective amount to i) induce or increase apoptosis of target cell types such as immune cells, particularly pro-inflammatory immune cells, synoviocytes and ii) increase the quantity of the anti-inflammatory regulatory T cells or a combination thereof. TRAIL is believed to have a therapeutic effect against RA by inducing apoptosis of activated lymphocytes or synoviocytes or increasing the population of the anti-inflammatory regulatory T cells. Therefore, in the most preferred embodiments, the TRAIL-conjugate is administered in an effective amount to induce or increase apoptosis of activated, pro-inflammatory lymphocytes, synoviocytes, or increase anti-inflammatory regulatory T cells, or a combination thereof Preferably, the level of apoptosis is effective to reduce or inhibit the onset or progression of an autoimmune disease such as rheumatoid arthritis, or one or more symptoms thereof. In some embodiments, the subject has rheumatoid arthritis and the method reduces, or prevents an increase, in joint swelling, joint pain, or a combination thereof.

In some embodiments, the method is effective to reduce, or prevent an increase, in one or more biochemical, physiological, or pathological indications of the autoimmune or inflammatory disease or disorder. For example, if the disease or disorder is rheumatoid arthritis, the TRAIL-conjugate can be administered in an effective amount to reduce, or prevent an increase, in joint swelling, erythema, joint rigidity, inflammatory cell infiltration into the joint(s), synovitis, pannus formation, destruction of articular cartilage, bone erosion, elevated erythrocyte sedimentation rates (ESR), anaemia and combinations thereof. Pro-inflammatory molecules can accelerate pannus formation and mediate cartilage and bone destruction (McInnes, et al., *Nature reviews Immunology*, 7(6):429-42 (2007); Feldmann, et al., *Annual review of immunology* 14:397-440 (1996). In some embodiments, the TRAIL-conjugate can reduce or prevent increases in expression of pro-inflammatory molecules, for example, TNF-α, IL-1β, IFN-γ, IL-2, IL-6, IL-17, ICAM-1, COX-2, iNOS, or combination thereof. In some embodiments, the TRAIL-conjugate is effective to reduce activated lymphocytes while increasing the population of the anti-inflammatory regulatory T cells. In some embodiments, the TRAIL-conjugate is effective to reduce, or prevent increases in, expression or circulating levels of autoantibodies to IgGFc (i.e., "rheumatoid factors (RF)"), antibodies to citrullinated peptides (ACPA), or combinations thereof. The levels of circulating pro-inflammatory molecules, autoantibodies, ect., can be measured in, for example, a blood, serum, or synovial fluid sample take from the subject before and again after administration to the TRAIL-conjugate.

The TRAIL-conjugate can also be effective to reduce, improve, or prevent more general symptoms of arthritis such as tender or warm joints, morning stiffness, bumps of tissue under the skin on the arms (rheumatoid nodules), fatigue, fever, weight loss, or combinations thereof.

Apoptosis and the resolution of symptoms can be assessed in the subject using a number of techniques. For example, overall improvement in the condition of the joints can be monitored over time. The joints or overall condition of the RA can be assessed, rated, staged, or evaluated using standard methods that are known in the art. See, for example, European League Against Rheumatism (EULAR) management guidelines, 2010 American College of Rheumatology (ACR)/EULAR classification criteria (Aletaha, et al., *Arthritis Rheum.*, 62(9):2569-81 (2010), 2012 ACR disease activity measures (Anderson, Arthritis Care Res (Hoboken), 64:640-7 (2012)), or 2011 ACR/EULAR definitions of remission. In preferred embodiments, the joints or over condition of the RA is improved overtime following administration of the TRAIL-conjugate.

The apoptosis of target cells can be determined from biopsies. Any change, and in particular any increase, in the frequency of apoptosis of target cells can be measured. Apoptotic cells can be identified using a number of well-known methods. Techniques such as TUNEL staining (terminal deoxynucleotidyl transferase mediated deoxyuridine trisphosphate nick end labelling) can be used to identify apoptotic cells. TUNEL staining is particular useful as it can be used to identify apoptotic cells in situ.

Other well-known techniques for identifying and/or quantifying apoptosis can be employed such as, for example, Annexin V staining, antibodies against single stranded DNA, caspase substrate assays, ligation mediated PCR and cell membrane permeability staining DNA fragmentation can be analyzed by gel electrophoresis. Staining can also be used to determine the morphological characteristics associated with apoptosis, such as membrane blebbing and the breakdown of the nucleus. Acridine orange staining can be used to identify apoptotoic cells. Cells may be stained with propidium iodide to analyze DNA content. Tests such as trypan blue staining can be used to check that the membrane cell is intact and that they are apoptotic not necrotic.

The effect of administration of the TRAIL-conjugate can be compared to a control. Suitable controls are known in the art and include, for example, a matched untreated subject, or a matched subject administered a therapeutic agent that does not induce or increase apoptosis of the target cells.

The compositions can be administered locally or systemically, as discussed above. However, preferably the composition is administered systemically.

The dosage and frequency of administration can depend on the TRAIL-conjugate that is selected. In some embodiments, the TRAIL-conjugate is administered systemically once, twice, or three times every 1, 2, 3, 4, 5, 6, 7, 8, 9, 10, 11, 12, 13, 14, 15, 16, 17, 18, 19, 20, 21, 28, or more days. Preferably the TRAIL-conjugate need only be administered once every 3, 4, 5, 6, 7, or more days. In the most preferred embodiments, the TRAIL-conjugate need only be administered once a week, once every 10 days, or once every two weeks.

As discussed above, and illustrated in the Examples below, a TRAIL-conjugate with 30 kDa PEG exhibit a longer duration of action than a TRAIL-conjugate with a 5 kDa PEG. More specifically, the 30K-PEG-TRAIL, was effective when administered once weekly, while the 5K-PEG-TRAIL was effective when administered once every third day. Therefore, the frequency of administration can be determined by the practitioner based on the structure of the TRAIL-conjugate.

Typically, the compositions disclosed herein are administered in a dosage of between about 0.01 and 1,000 mg/kg, or between about 1 and 100 mg/kg, 5-50 mg/kg, or 10-20 mg/kg.

As reported by Herbst, et al., *J. Clin. Oncol.* 2010 10; 28(17):2839-46, in a phase I, open-label, dose-escalation study treated patients with advanced cancer with rhApo2L/TRAIL doses ranging from 0.5 to 30 mg/kg/d, with parallel dose escalation for patients without liver metastases and with normal liver function (cohort 1) and for patients with liver metastases and normal or mildly abnormal liver function (cohort 2). Doses were given daily for 5 days, with cycles repeating every 3 weeks.

In the Examples below, mice were administered PEG-TRAIL conjugates at a dosage of 300 μg/mouse once every 3 days, or once weekly. For a 25 gram mouse, this is approximately 12 mg/kg. In some embodiments, the estimated mouse dosage is extrapolated to a human dose through normalization to body surface area as discussed in Reagan-Shaw, et al., *The FASEB Journal*, 22:1-3 (2007) (the FASEB *Journal article fj.*07-9574LSF). Therefore, in some embodiments, the dosage is about 1-1,000 mg/m$^2$, or 10-100 mg/m$^2$, or 25-75 mg/m$^2$, or 40-60 mg/m$^2$ or about 45 mg/m$^2$.

IV. Combination Therapies

One or more of the TRAIL-conjugates disclosed herein, and compositions thereof, can be administered to subjects in need thereof alone, or in combination, with one or more additional active agents.

A. Additional Active Agents

Additional agents can be proteins, peptides, carbohydrates, nucleic acids, lipids, small molecules, or combinations thereof. In some embodiments, the second active agent is an agent that is known in the art for treatment of autoimmune disease, particularly rheumatoid arthritis. As discussed in more detail below, standard therapy for RA includes analgesics, non-steroidal anti-inflammatory drugs, and biologic disease-modifying anti-rheumatic drugs (DMARDs) that target components of the immune response. Some such therapies target excessive inflammatory mediators, released by infiltrating lymphocytes that are responsible for joint destruction. As a result, anti-cytokine RA therapeutics have been identified such as tumor necrosis factor alpha (TNF-α) and interleukin (IL)-1 receptor antagonistic antibodies. In 2012, *Interleukin* (IL) targets made up 15%, kinase inhibitors made up 12%, B-cell targets made up 9% and TNF inhibitors made up 7% of the products in the RA drug class. TNF-α antagonist are considered by some to be the most efficient of conventional biologics to treat RA (Audo, et al., *Cytokine*, 63(2):81-90 (2013)). Others targets in the TNF family implicated in RA include receptor activator for nuclear factor kappa-beta ligand (RANKL) and its receptor RANK, and osteoprotegerin (OPG) (Lamhamedi-Cherradi, et al., *Nature immunology* 4(3):255-60 (2003)).

Therefore, the second active agent can be one that modulates immune cells, particularly lymphocytes, synoviocytes, or a combination thereof. The active agent can reduce or inhibit the proliferation or activity of pro-inflammatory immune cells, induce or increase the proliferation or activity of anti-inflammatory immune cells (e.g., regulatory T cells), reduce or inhibit the proliferation or activity of synoviocytes, or any combination thereof. In some embodiments, the second active agent reduces the expression or circulation of one or more pro-inflammatory molecules, including, but not limited to TNF-α, IL-1β, IFN-γ, IL-2, IL-6, IL-8, IL-1β, TGF-β, IL-17, IL-6, IL-23, IL-22, IL-21, prostanoids, and matrix metalloproteinases (MMPs). For example, in some embodiments, the second active agent is one that reduces the level of one or more pro-inflammatory molecules in the blood, serum, or synovial fluid when administered to a subject with RA.

1. Conventional Treatments for Rheumatoid Arthritis

In some embodiments, the TRAIL-conjugates are administered in combination with a conventional treatment or agent used for treating or preventing rheumatoid arthritis. Common RA drugs can be divided into two general classes: fast-acting "first-line drugs" and slow-acting "second-line drugs" (also referred to as disease-modifying antirheumatic drugs or DMARDs).

a. First-Line Drugs

The TRAIL-conjugates can be administered in combination with a first-line drug for treating rheumatoid arthritis.

The first-line drugs, such as aspirin and cortisone (corticosteroids), are typically agents that reduce pain, inflammation, or a combination thereof. For example, the first-line drug can be a nonsteroidal anti-inflammatory drugs (NSAIDs). N-Acetyl salicylate (aspirin), naproxen (NAPROSYN®), ibuprofen (ADVIL®, MEDIPREN®, MOTRIN®), and etodolac (LODINE®) are examples of NSAIDs. NSAIDs are medications that can reduce tissue inflammation, pain, and swelling. NSAIDs are not cortisone.

Aspirin, in doses higher than those used in treating headaches and fever, is also effective anti-inflammatory medication for rheumatoid arthritis. However, NSAIDs are typically as effective as aspirin in reducing inflammation and pain and require fewer dosages per day.

The most common side effects of aspirin and other NSAIDs include stomach upset, abdominal pain, ulcers, and even gastrointestinal bleeding. Therefore, NSAIDs can be taken with additional medications that are frequently recommended to protect the stomach from their ulcer effects. These medications include antacids, sucralfate (CARAFATE®), proton-pump inhibitors (PREVACID® and others), and misoprostol (CYTOTEC®). NSAIDs can also be selective Cox-2 inhibitors, such as celecoxib (CELEBREX®), which offer anti-inflammatory effects with less risk of stomach irritation and bleeding risk.

Corticosteroid medications can be given orally or injected directly into tissues and joints. They are more potent than NSAIDs in reducing inflammation and in restoring joint mobility and function, and often administered to treat severe flair-ups or when the subject is not responsive to NSAIDs. Corticosteroid medications can be administered with calcium and/or vitamin D supplements to reduce or prevent osteoporosis.

b. Second-Line Drugs

The TRAIL-conjugates can be administered in combination with a second-line drug for treating rheumatoid arthritis. While first-line medications can relieve joint inflammation and pain, they do not necessarily prevent joint destruction or deformity. Rheumatoid arthritis requires medications other than NSAIDs and corticosteroids to stop progressive damage to cartilage, bone, and adjacent soft tissues. The medications that target the mechanisms underlying the disease are also referred to as disease-modifying antirheumatic drugs (DMARDs).

Second-line agents, also sometimes referred to as slow-acting medicines, may take weeks to months to become effective. They are typically administered for long periods of time, even years, at varying doses. DMARDs can promote remission by reducing the progression of joint destruction and deformity. Sometimes a number of DMARD second-line medications are used together as combination therapy. Therefore, in some embodiments, the TRAIL-conjugate is administered two or more second-line drugs.

Hydroxychloroquine (PLAQUENIL®); sulfasalazine (AZULFIDINE®); gold salts such as gold thioglucose (SOLGANAL®); gold thiomalate (MYOCHRYSINE®); oral gold (e.g., auranofin (ridaura)); d-penicillamine (DEPEN®, CUPRIMINE®); immunosuppressives such as methotrexate, azathioprine (IMURAN®), cyclophosphamide (CYTOXAN®), chlorambucil (LEUKERAN®), and cyclosporine (SANDIMMUNE®); leflunomide (ARAVA®); etanercept (ENBREL®); infliximab (REMICADE®); anakinra (KINERET®); adalimumab (HUMIRA®); rituximab (RITUXAN®); abatacept (ORENCIA®); golimumab (SIMPONI®); certolizumab pegol (CIMZIA®); tocilizumab (ACTEMRA®); and tofacitinib (XELJANZ®).

In some embodiments, the TRAIL-conjugates are administered in combination with a tumor necrosis factor (TNF)-α antagonist. TNF-α antagonists are currently the most effective, efficient and common biologics used to treat RA. Common TNF-α antagonists include, but are not limited to, etanercept, infliximab, adalimumab, golimumab, and certolizumab pegol. These drugs typically work by intercepting tumor necrosis factor or TNF in the joints and reducing its pro-inflammatory signal. This in turn reduces the recruitment of pro-inflammatory cells to the site of inflammation. Etanercept is typically injected subcutaneously once or twice a week. Infliximab can be given by infusion directly into a vein (intravenously). Adalimumab is typically injected subcutaneously either every other week or weekly. Golimumab is typically injected subcutaneously on a monthly basis. Certolizumab pegol is typically injected subcutaneously every two to four weeks. They are also frequently used in combination with methotrexate and other DMARDs. Furthermore, it should be noted that the TNF-blocking biologics all are more effective when combined with methotrexate. These medications should be avoided by people with significant congestive heart failure or demyelinating diseases (such as multiple sclerosis) because they can worsen these conditions.

In some embodiments, the effect of administering a TRAIL-conjugate and a TNF-α antagonist in a combination therapy is more than the additive effect of administering the two agents as monotherapies.

In some embodiments, the TRAIL-conjugate is administered in combination with adjunct therapy, for example, surgery or apheresis. Apheresis is a procedure that involves removing whole blood from a donor or patient and separating the blood into individual components so that one or more particular component can be removed. In the case of rheumatoid arthritis, apheresis is most typically used to remove autoantibodies that contribute to disease progression. Following apheresis, the remaining blood components then are re-introduced back into the bloodstream of the patient or donor.

2. Chemotherapeutic Agents

TRAIL receptor agonists have been investigated for use in the treatment of cancer, both alone and in combination with conventional cancer treatments such as chemotherapeutic agents. Some reports indicate that chemotherapeutic drugs can sensitize cells to TRAIL-induced apoptosis, and some results indicate the combination of the two agents is more effective than the sum of effects of the agents when used alone (Cuello, et al., *Gynecol Oncol.*, 81(3):380-90 (2001) Wu, et al., *Vitam Horm.*, 67:365-83 (2004)). Therefore, in some embodiments, the subjects and diseases disclosed herein are treated with a combination of a TRAIL-conjugate and a chemotherapeutic agent. In some embodiments, the subjects do not have cancer.

Exemplary chemotherapeutic drugs include, but are not limited to, doxorubicin, 5-fluorouracil, cisplatin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

B. Dosage and Treatment Regimes for Combination Therapies

The methods of treatment disclosed herein typically include treatment of a disease or symptom thereof, or a method for achieving a desired physiological change, including administering to an animal, such as a mammal, especially a human being, an effective amount of a TRAIL-conjugate disease or symptom thereof, or to produce the physiological change. In some embodiments, the TRAIL-conjugate is in combination with an additional active agent, such as those discussed above. The TRAIL-conjugate and the additional active agent can be administered together, such as part of the same composition, or administered separately and independently at the same time or at different times (i.e., administration of the TRAIL-conjugate and the second active agent is separated by a finite period of time from each other). Therefore, the term "combination" or "combined" is used to refer to either concomitant, simultaneous, or sequential administration of the ligand or agonist and the second active agent. The combinations can be administered either concomitantly (e.g., as an admixture), separately but simultaneously (e.g., via separate intravenous lines into the same subject; one agent is given orally while the other agent is given by infusion or injection, etc.), or sequentially (e.g., one agent is given first followed by the second).

In preferred embodiments, administration of the TRAIL-conjugate in combination with the second active agent achieves a result greater than when the TRAIL-conjugate and the second active agent are administered alone or in isolation (i.e., the result achieved by the combination is more than additive of the results achieved by the individual components alone). In some embodiments, the effective amount of one or both agents used in combination is lower than the effective amount of each agent when administered separately. In some embodiments, the amount of one or both agents when used in the combination therapy is sub-therapeutic when used alone.

A treatment regimen of the combination therapy can include one or multiple administrations of the TRAIL-conjugate. A treatment regimen of the combination therapy can include one or multiple administrations of the second active agent.

In some embodiments, the TRAIL-conjugate is administered prior to the first administration of the second active agent. In other embodiments, the ligand or agonist is administered after to the first administration of the second active agent.

The TRAIL-conjugate can be administered at least 1, 2, 3, 5, 10, 15, 20, 24 or 30 hours or days prior to or after administering of the second active agent.

Dosage regimens or cycles of the agents can be completely, or partially overlapping, or can be sequential. For example, in some embodiments, all such administration(s) of the TRAIL-conjugate occur before or after administration of the second active agent. Alternatively, administration of one or more doses of the TRAIL-conjugate can be temporally staggered with the administration of second therapeutic agent to form a uniform or non-uniform course of treatment whereby one or more doses of TRAIL-conjugate are administered, followed by one or more doses of second active agent, followed by one or more doses of TRAIL-conjugate; or one or more doses of second active agent are administered, followed by one or more doses of the TRAIL-conjugate, followed by one or more doses of second active agent; etc., all according to whatever schedule is selected or desired by the researcher or clinician administering the therapy.

An effective amount of each of the agents can be administered as a single unit dosage (e.g., as dosage unit), or sub-therapeutic doses that are administered over a finite time interval. Such unit doses may be administered on a daily basis for a finite time period, such as up to 3 days, or up to 5 days, or up to 7 days, or up to 10 days, or up to 15 days or up to 20 days or up to 25 days The present invention will be further understood by reference to the following non-limiting examples.

EXAMPLES

Example 1

PEG-TRAIL Analogs Induce Apoptosis of Jurkat Cells and Down-Regulate Inflammatory Molecules Materials and Methods Two different PEGylated TRAIL analogs, trimeric active TRAIL having PEG, with molecular weight of 5 kDa and 30 kDa, at the N-terminal site were prepared. Briefly, monomethoxy PEG-aldehyde (mPEG-ALD with molecular weight of 5 kDa and 30 kDa) (Nippon Oil Fats, NOF, Tokyo) was conjugated to the N-terminal site of TRAIL having a trimer-forming zipper domain, in the presence of 20 mM sodium cyanoborohydrice (NaCNBH$_3$) in 50 mM sodium acetate buffer at pH 5, as described previously (U.S. Patent Application No. 20090203599 and Chae, et al., *Molecular Cancer Therapeutics*, 9(6):1719-29 (2010), Kim, et al., *Bioconjugate Chemistry*, 22(8):1631-1637 (2011

PEG and TRAIL molar ratios and reaction times were studied by size exclusion chromatography monitoring. PEG-TRAIL analogs were purified and concentrated by gel-filtration chromatography and ultrafiltration, respectively, and stored at −20° C. until use. Analogs were characterized and identified as described.

The in vitro cytotoxicities of PEG-TRAIL analogs were examined in Jurkat cells using an established MTS-based assay and Annexin-V-FLUOS staining Human leukemia T-cell line Jurkat cells were cultured at a cell density of $4\times10^6$ cells/ml (100 µl/well) in 96-well plates, and stimulated with 10 ng/ml Con A (concanavalin A) for 12 h.

Pre-determined amounts of PEG-TRAIL were then added to final concentrations of 0-10,000 ng/ml, and incubated for 24 h. MTS assays (CellTiter 96 Aqueous Non-Radioactive Cell Proliferation Assay; Promega, Madison, Wis.) were performed on collected culture supernatants following manufacturer's protocol. Cell viabilities (%) were calculated by expressing the absorbance at 490 nm of treated samples as percentages of those of untreated controls. To examine the apoptotic effect on Jurkat cells, Annexin-V-FLUOS staining kits (Roche Diagnostics, Mannheim, Germany) was used according to manufacturer's protocol. In brief, Jurkat cells were treated with Con A and PEG-TRAIL (500 ng/ml) as described above, and then washed with PBS and stained with 100 μl of an Annexin-V/propidium iodide mixture for 15 min. Finally, apoptotic and necrotic cells levels were analyzed by fluorescence microscopy. Apoptotic effects (%) were calculated by expressing number of stained cells (green or orange) as percentages of total cells.

The effect of PEG-TRAIL analogs on down-regulating inflammatory molecules in Jurkat cells was analyzed at the molecular level by Western blotting and quantitative real-time PCR (qPCR) after incubating the cells with PEG-TRAIL at the concentrations of 0, 0.1, 1, 10, 100 and 1000 ng/mL for 24 h. Anti-Caspase-8 (Cell Signaling Technology, Danvers), anti-cleaved Caspase-8, anti-cleaved Caspase-3 (Cell Signaling Technology), anti-Cox-2 and anti-ICAM-1, anti-GAPDH (Santa Cruz Biotechnology) were used in Western blot analysis. In general, cells were lysed by sonication in ice-cold PBS buffer containing protease inhibitor (1 mM PMSF and 1 mg/mL each of aprotinin, leupeptin and pepstatin A). Cell lysates were clarified by centrifugation and the supernatants were used to measure protein concentration by Braford assay (Bio-Rad Laboratories, Hercules, Calif.). The samples were subjected to electrophoresis through SDS-polyacrylamide gels and transferred to nitrocellulose membrane. After blocking the membrane with 3% bovine serum albumin (BSA, Sigma), the membranes were incubated with the primary antibodies overnight. GAPDH was used for protein loading control. Protein bands were detected using a secondary antibody conjugated with horseradish peroxidase (Thermo) and a chemiluminescence detection system (ECL) onto X-ray film. The intensity of protein bands was quantified by Multi Gauge software (Fujifilm). For qPCR studies, total RNA from cultured cells was extracted with TRIzol reagent (Life Technologies, Grand Island, N.Y.) following the instruction provided by the company. RNA concentration was measured spectrophotometrically by using NanoDrop 2000 (Thermo Fisher Scientific, Waltham, Mass.). 1 μg of total RNAs were reverse-transcribed to cDNA using the High-Capacity cDNA Reverse Transcription System (Life Technologies). Comparative qPCR was performed in duplicate or triplicate for each sample using fast SYBR Green Master Mix (Life Technologies) and StepOnePlus Real-Time PCR System (Life Technologies). The expression levels of target genes were normalized to the expression of GAPDH and calculated based on the comparative cycle threshold Ct method. The sequence of the primers were used as follows;

Murine IFN-γ
(SEQ ID NO: 6)
5'-CAGCAACAGCAAGGCGAAA-3' (Forward), (SEQ ID NO: 7)
5'-CTGGACCTGTGGGTTGTTGAC-3' (Reverse);

Murine ICAM-1
(SEQ ID NO: 8)
5'-GTGGCGGGAAAGTTCCTG-3' (Forward), (SEQ ID NO: 9)
5'-CGTCTTGCAGGTCATCTTAGGAG-3' (Reverse);

Murine Cox-2
(SEQ ID NO: 10)
5'-TGCCTGGTCTGATGATGTATGCCA-3' (Forward), (SEQ ID NO: 11)
5'-AGTAGTCGCACACTCTGTTGTGCT-3' (Reverse);

Murine iNOS
(SEQ ID NO: 12)
5'-CCTGGTACGGGCATTGCT-3' (Forward), (SEQ ID NO: 13)
5'-GCTCATGCGGCCTCCTTT-3' (Reverse);

Murine GAPDH
(SEQ ID NO: 14)
5'-CGACTTCAACAGCAACTCCCACTCTTCC-3' (Forward), (SEQ ID NO: 15)
5'-CCTTCTCACCCTCAACGACAACTTCAGC-3' (Reverse).

Results

Figure 1B:
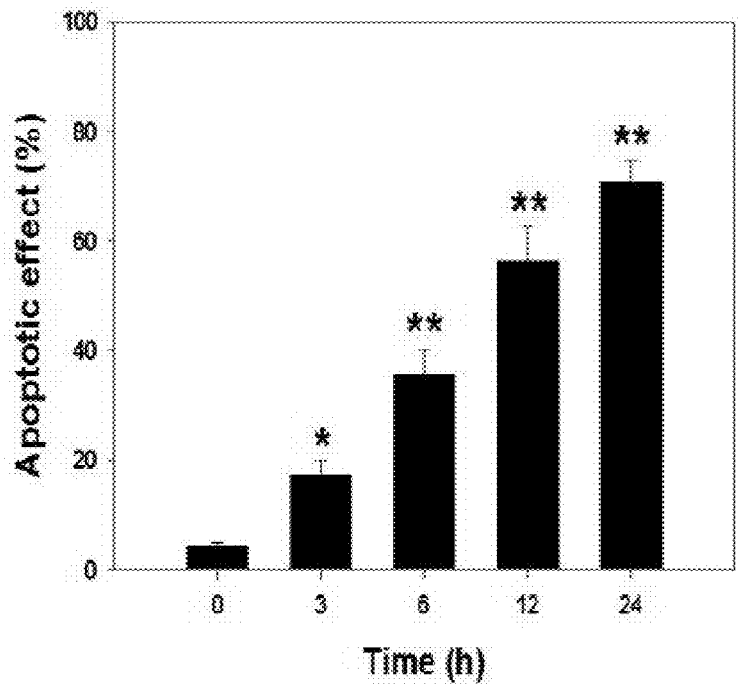
FIG. 1B is a bar graph showing time-dependent (hours) Jurkat cell apoptosis (Apoptotic Effect (%)) after treatment with 30K-PEG-TRAIL at 500 ng/mL as determined by Annexin-V-FLUOS staining Data are expressed as means±SEMs of triplicate cultures. *$p<0.05$ or **$p<0.01$ versus apoptotic cells at time 0.

TRAIL and PEG-TRAIL analogs demonstrated marked apoptotic effects on Jurkat cells as evident by MTS assay ($IC_{50}$ for TRAIL, 5K-PEG-TRAIL and 30K-PEG-TRAIL, 4.89 ng/mL, 15.71 ng/mL, and 68.26 ng/mL, respectively; FIG. 1A). In addition, time-dependent apoptotic cell death was investigated by Annexin-V-FLUOS staining Typically, after 24 h of 30K-PEG-TRAIL treatment (500 ng/ml), more than 70% Jurkat cells were committed to apoptosis (FIG. 1B).

Western blot analyses confirmed that 5K-PEG-TRAIL-treated (1,000 ng/mL) Jurkat cells significantly upregulated expression levels of apoptotic markers, cleaved caspase-8 and cleaved caspase-3, by 4.7-fold and 3.9-fold, respectively, compared to non-treated cells ($p<0.05$). In addition, 5K-PEG-TRAIL declined expression levels of inflammatory molecules, COX-2 and ICAM-1 by 54% and 12%, respectively, compared to non-treated cells ($p<0.05$). qPCR of mRNA obtained from 5K-PEG-TRAIL-treated Jurkat cells revealed more than 50% reduction of ICAM-1, iNOS and IFN-γ expressions compared to non-treated cells (for ICAM-1, IFN-γ, 50%, 82%, 75%, respectively, vs. non-treated cells, $p<0.05$). These results indicate that PEG-TRAIL induces death receptor-mediated apoptosis in activated T cells while inhibiting the regulation of inflammatory markers such as ICAM-1, COX-2 and iNOS.

Example 2

5K-PEG-TRAIL Reduces the Severity of Collagen-Induced Arthritis (CIA)

Materials and Methods

Collagen induced arthritis was subjected in DBA/1 mice as described by Jin et al, *J. Pharmacol. Exp. Ther.* 332(3): 858-865 (2010). Bovine type II collagen (CII, 2 mg/mL; Chondrex, Inc., Redmond, Wash.) was emulsified in an equal volume of Complete Freund's adjuvant (Chondrex, Inc.) in an ice-cold water bath. First, Male DBA/1J mice were immunized subcutaneously at the base of the tail with 0.1 ml of the emulsion at day 0. On day 21, mice received a booster immunization (0.1 ml) using the same procedure but with Incomplete Freund's Adjuvant (IFA; Chondrex).

Clinical severities of arthritis were assessed visually every other day in wrist and ankle joints under blinded conditions. TRAIL and 5K-PEG-TRAIL were diluted in phosphate buffered saline solution (PBS) at the intended protein concentrations. Mice were i.p. administered TRAIL (daily or every 3 days at 300 μg/mouse/day) or 5K-PEG-TRAIL (daily, every 3 days, or weekly at 300 μg/mouse/day) (300 μl) after 1 day from the booster immunization to the end of experiment. PBS was administered as a negative control. Arthritis was graded using clinical signs on a 0-4 scale as follows: 0=normal, 1=slight swelling and edema, 2=moderate swelling and edema, 3=severe swelling and pronounced edema, and 4=joint deformity or ankylosis. Each limb was graded with the maximum possible score being 16 per mouse. Clinical scores were monitored throughout the entire treatment.

Results

Figure 2A:
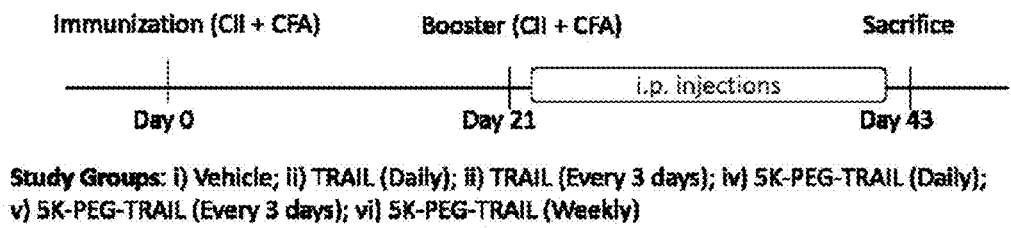
FIG. 2A is a schematic showing an assay designed to test the effect of TRAIL and TRAIL analog dosing interval on the development and progression of experimental RA (collagen-induced arthritis (CIA) in DBA/1J mice).
Figure 2B:
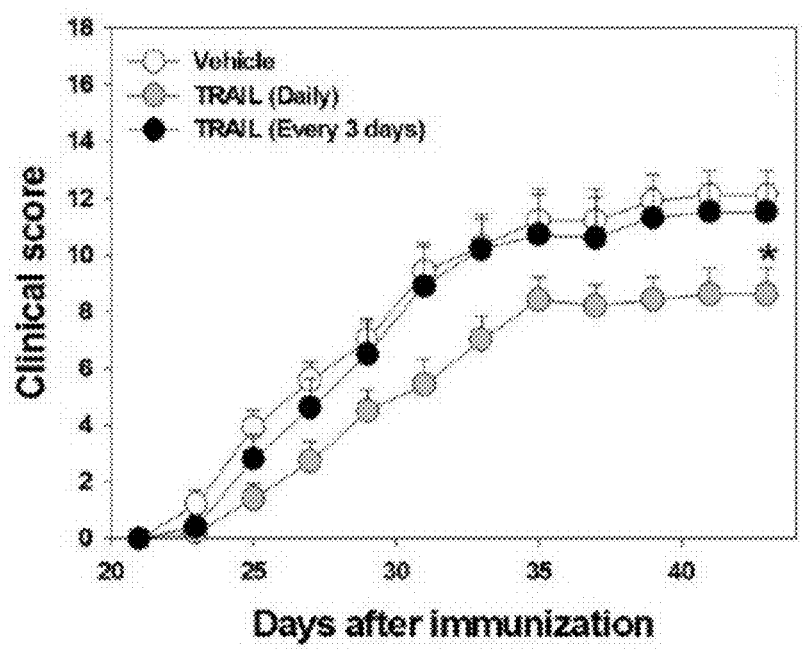
FIG. 2B is a line graph showing the effect of vehicle, or daily, or every third day administration of 300 μg/mouse/day of TRAIL on the clinical score of CIA over time (days after immunization).
Figure 2C:
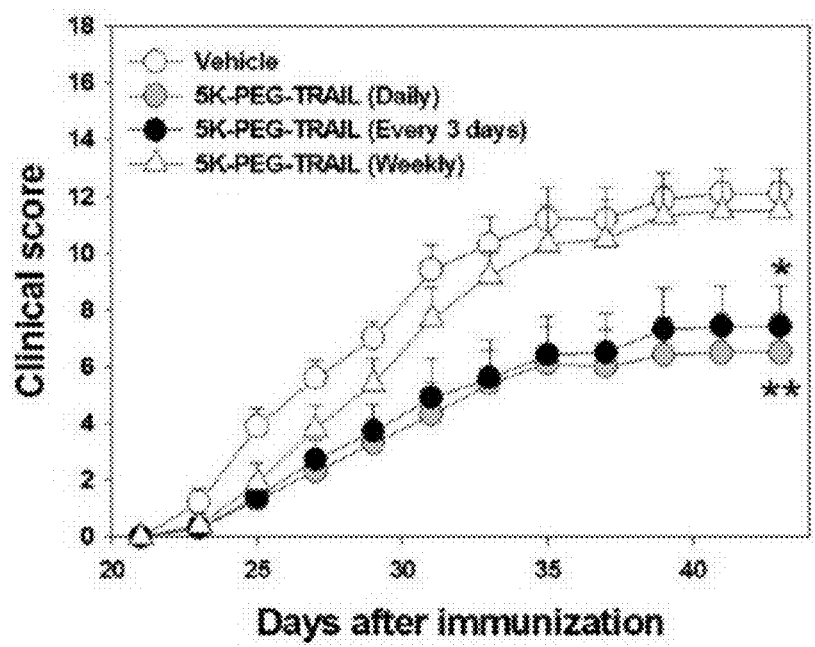
FIG. 2C is a line graph showing the effect of vehicle, or daily, or every third day, or once weekly administration of 300 μg/mouse/day of 5K-PEG-TRAIL on the clinical score of CIA over time (days after immunization). Data are expressed as means±SEMs (n=10 per group). Statistical significance; *$p<0.05$ or **$p<0.01$ versus vehicle-treated CIA mice.

To investigate the effect of the dosing interval on the development and progression of collagen-induced arthritis (CIA), mice were i.p. administered TRAIL (daily or every 3 days) or 5K-PEG-TRAIL (daily, every 3 days, or weekly, 300 μg/mouse/day) and therapeutic effects were continuously monitored. CIA developed rapidly in mice immunized with bovine type II collagen (CII), and clinical signs of the disease (periarticular erythema and edema) first appeared in hind paws at approximately 23 days post-CI. All vehicle-treated mice were affected by day 25 (FIGS. 2B and 2C). Hind paw erythema and swelling increased in frequency and severity in a time-dependent manner, and a mean maximum clinical score was reached between 35 and 39 days post-CI.

Although TRAIL administered every 3 days produced no significant difference as compared with CIA mice (PBS treatment), mice treated daily with TRAIL improved (FIG. 2B). In the case of daily and every 3 day administered 5K-PEG-TRAIL, significant therapeutic effects were observed, whereas weekly injections had no evident therapeutic effect (FIG. 2C). In addition, a comparison of daily TRAIL and 5K-PEG-TRAIL revealed that 5K-PEG-TRAIL had a better therapeutic effect (clinical scores of 8.6±0.90 and 6.5±1.38 at day 41, respectively, FIG. 2C).

Example 3

5K-PEG-TRAIL reduces pro-inflammatory cytokines and increases the quantity of the anti-inflammatory regulatory T cells in CIA models Materials and Methods Protein was extracted using T-PER tissue protein extraction buffer containing a protease inhibitor cocktail (Roche). Briefly, 20 μg of proteins were separated by SDS-PAGE and transferred to PVDF membranes. Membranes were blocked in 5% non-fat milk for 1 h at room temperature and incubated overnight at 4° C. and analyzed with antibodies raised against DR5 (Abcam, Cambridge, UK), Caspase-8 (Cell Signaling), cleaved Caspase-3 (Cell Signaling), COX-2 (Santacruz), ICAM-1 (Santacruz), p-p65 (Cell Signaling), or GAPDH (Santacruz). Protein bands were detected using a secondary antibody and a chemiluminescence detection system as described. For qPCR studies, total RNAs were isolated and analyzed as described in Example 1. The sequence of the primers were used as follows;

Murine TNF-α
(SEQ ID NO: 16)
5'-TCTCATGCACCACCATCAAGGACT-3' (Forward), (SEQ ID NO: 17)
5'-ACCACTCTCCCTTTGCAGAACTCA-3' (Reverse);

Murine IFN-γ
(SEQ ID NO: 6)
5'-CAGCAACAGCAAGGCGAAA-3' (Forward), (SEQ ID NO: 7)
5'-CTGGACCTGTGGGTTGTTGAC-3' (Reverse);

Murine IL-1β
(SEQ ID NO: 18)
5'-CAACCAACAAGTGATATTCTCCATG-3' (Forward), (SEQ ID NO: 19)
5'-GATCCACACTCTCCAGCTGCA-3' (Reverse);

Murine IL-6
(SEQ ID NO: 20)
5'-GGTGACAACCACGGCCTTCCC-3' (Forward), (SEQ ID NO: 21)
5'-TTAAGCCTCCGACTTGTGAAGTGGT-3' (Reverse);

Murine IL-17
(SEQ ID NO: 22)
5'-GCTCCGAAGGCCCTCAGA-3' (Forward), (SEQ ID NO: 23)
5'-CTTTCCCTCCGCATTGACA-3' (Reverse);

Murine TGF-β1
(SEQ ID NO: 24)
5'-TGACGTCACTGGAGTTGTACGG-3' (Forward), (SEQ ID NO: 25)
5'-GGTTCATGTCATGGATGGTGC-3' (Reverse);

Murine IL-10
(SEQ ID NO: 26)
5'-ATTTGAATTCCCTGGGTGAGAA-3' (Forward), (SEQ ID NO: 27)
5'-ACACCTTGGTCTTGGAGCTTATTAA-3' (Reverse).

Murine ICAM-1
(SEQ ID NO: 8)
5'-GTGGCGGGAAAGTTCCTG-3' (Forward), (SEQ ID NO: 9)
5'-CGTCTTGCAGGTCATCTTAGGAG-3' (Reverse);

Murine Cox-2
(SEQ ID NO: 10)
5'-TGCCTGGTCTGATGATGTATGCCA-3' (Forward), (SEQ ID NO: 11)
5'-AGTAGTCGCACACTCTGTTGTGCT-3' (Reverse);

Murine iNOS
(SEQ ID NO: 12)
5'-CCTGGTACGGGCATTGCT-3' (Forward), (SEQ ID NO: 13)
5'-GCTCATGCGGCCTCCTTT-3' (Reverse);

Murine GAPDH
(SEQ ID NO: 14)
5'-CGACTTCAACAGCAACTCCCACTCTTCC-3' (Forward), (SEQ ID NO: 15)
5'-CGACTTCAACAGCAACTCCCACTCTTCC-3' (Reverse).

Data were analyzed according to the comparative CT method and were normalized to GAPDH expression.

For analysis of the regulatory T (Treg) cell population, splenocytes of PEG-TRAIL-treated mice were stained with anti-CD4-FITC and CD25-APC antibodies (BDbioscience). After fixation and permeabilziation, stained splenocytes were incubated with anti-Dox3-PE antibody (BDbioscience). Treg (CD4+CD25+Foxp3+) percentages were determined using FACSCalibur (BDbioscience).

Results

To investigate the effect of systemically injected 5K-PEG-TRAIL on RA in CIA mice at molecular level, various inflammatory, pro-inflammatory and anti-inflammatory markers were analyzed. In CIA models, Western blot and qPCR analysis confirmed significantly upregulated inflammatory makers including ICAM-1, COX-2 and iNOS and pro-inflammatory cytokines such as TNF-α, IL-1β, INF-γ, IL-6, IL-17. In contrast, when 5K-PEG-TRAIL was systemically, those inflammatory and pro-inflammatory markers were significantly reduced (Table 1). Relative mRNA expressions expressed as fold-change are described in Table 1.

TABLE 1

Relative mRNA expression obtained from normal, CIA mice and 5K-PEG-TRAIL-treated CIA mice. Values are mean (s.e.m) (n = 8-10).

| Molecules | Control (normal mice) | CIA mice (Saline) | CIA mice + PEG-TRAIL |
|---|---|---|---|
| ICAM-1 | 1.0 (0.1) | 3.5 (0.5)## | 2.5 (0.2)* |
| COX2 | 1.0 (0.1) | 7.5 (1.7)## | 2.8 (0.3)** |
| iNOS | 1.1 (0.1) | 2.3 (0.4)## | 1.3 (0.2)** |
| TNF-α | 1.0 (0.1) | 4.1 (0.7)# | 2.4 (0.2)* |
| IFN-γ | 1.0 (0.1) | 3.5 (0.5)## | 2.0 (0.3)** |
| IL-1β | 1.0 (0.1) | 1.9 (0.2)## | 1.4 (0.1)* |
| IL-6 | 1.2 (0.2) | 11.3 (4.0)# | 3.7 (0.4)* |
| IL-17 | 1.1 (0.2) | 10.6 (4.2)# | 2.1 (0.2)* |

$p < 0.05$,
$p < 0.01$ versus Control mice;
*$p < 0.05$,
**$p < 0.01$ versus CIA mice In addition to down-regulating expressions of inflammatory and pro-inflammatory makers, PEG-TRAIL also increased the population of Foxp3+ regulatory T (Treg) cells (30% vs. CIA mice) while up-regulating anti-inflammatory cytokines, TGF-β1 and IL-10 by 1.4-fold and 21.9-fold, respectively, compared to that of non-PEG-TRAIL-treated CIA mice. These results clearly indicate enhanced therapeutic efficacy of systemically injected, long-acting PEG-TRAIL in CIA mice. The reduced clinical and histologic scores in Example 2 are related to reduced levels of inflammatory and pro-inflammatory makers and increased levels of anti-inflammatory Treg cells and cytokines such as TGF-β and IL-10 mainly induced by PEG-TRAIL.

Example 4

Weekly Dosing of 30K-PEG-TRAIL Reduces the Severity of CIA

Materials and Methods

TRAIL, 5K-PEG-TRAIL, and 30K-PEG-TRAIL were diluted in phosphate buffered saline solution (PBS) at the intended protein concentrations. CIA mice, prepared as described above, were i.p. administered TRAIL and TRAIL-conjugate weekly at 300 µg/mouse/day (300 µl) after 1 day from the booster immunization to the end of experiment. PBS was administered as a negative control. The experiment continued to 43 days after immunization. Arthritis was graded using clinical signs on a 0-4 scale as described.

Results

Figure 3A:
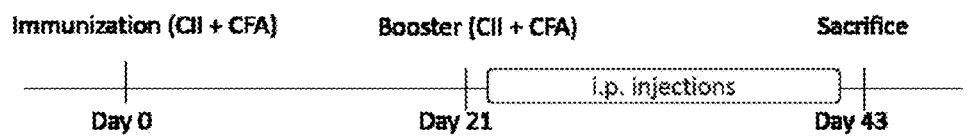
FIG. 3A is a schematic showing an assay designed to test the effect of PEG molecular weight of 5K-PEG and 30K-PEG TRAIL analogs on the development and progression of experimental RA (collagen-induced arthritis (CIA) in DBA/1J mice).
Figure 3B:
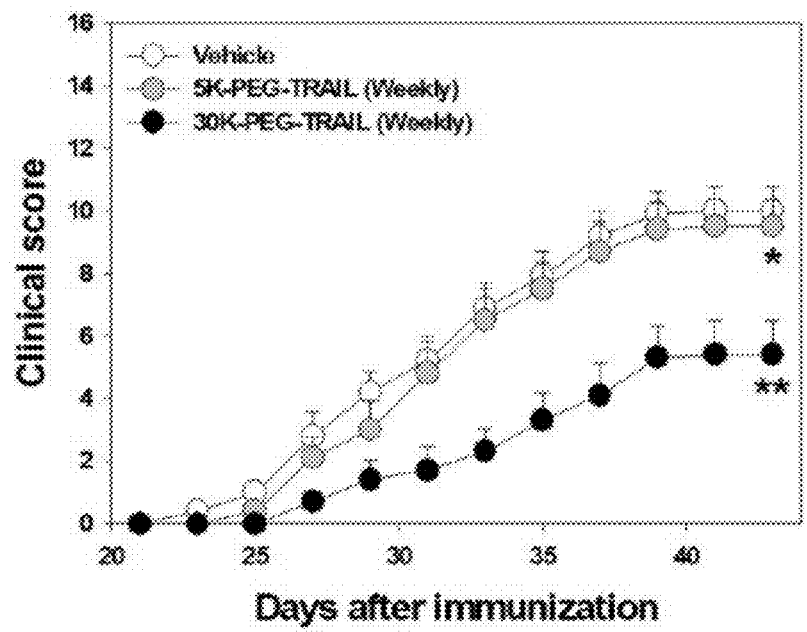
FIG. 3B is a line graph showing the effect of weekly administration of 300 μg/mouse/day of vehicle, 5K-PEG or 30K-PEG TRAIL analogs on the clinical score of CIA over time (days after immunization).
Figure 3C:
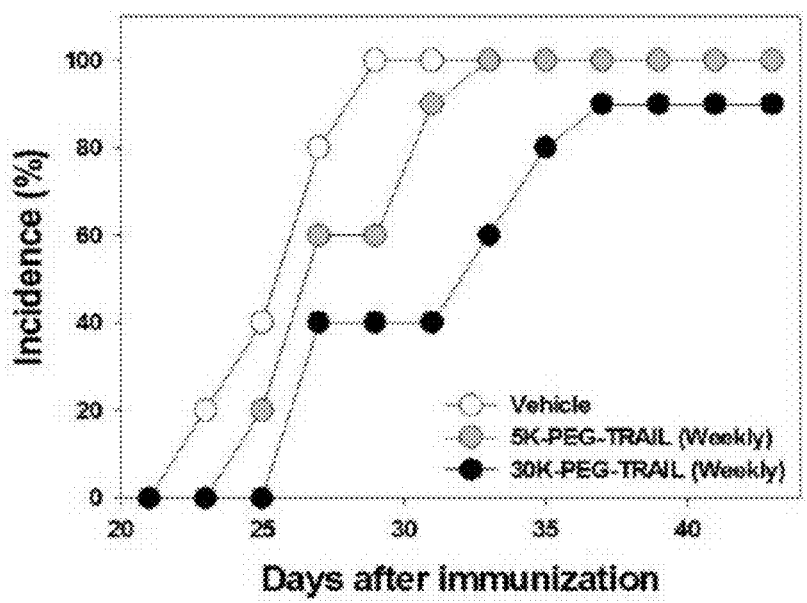
FIG. 3C is a line graph showing the effect of weekly administration of 300 µg/mouse/day of vehicle, 5K-PEG or 30K-PEG TRAIL analogs on the incidence (%) of CIA over time (days after immunization). Data are expressed as means±SEMs (n=10 per group). Statistical significance; *p<0.05 or **p<0.01 versus vehicle-treated CIA mice.

To investigate the effect of PEG molecular weight on the development and progression of CIA, mice were i.p. administered 5K-PEG-TRAIL or 30K-PEG-TRAIL (weekly, 300 µg/mouse/day) and therapeutic effects were continuously monitored. CIA developed rapidly in mice immunized with CII, and clinical signs of the disease (periarticular erythema and edema) first appeared in hind paws at approximately 23 days post-CI, and all vehicle-treated mice were affected by day 25 (FIG. 2B). Hind paw erythema and swelling increased in frequency and severity in a time-dependent manner, and a mean maximum clinical score was reached between 35 and 39 days post-CI. In the case of weekly administered 30K-PEG-TRAIL, significant therapeutic effects were observed, whereas weekly injections of 5K-PEG-TRAIL had no evident therapeutic effect (FIG. 3B). In addition, a comparison of clinical scores of weekly 5K-PEG-TRAIL and 30K-PEG-TRAIL revealed that 30K-PEG-TRAIL had a better therapeutic effect (clinical scores of 9.2±1.34 and 4.9±0.86 at day 41, respectively).

Treated joints were investigated using micro-computed tomographic (micro-CT) and histological techniques. In the reconstructed three-dimensional micro-CT images of the paw of a mouse with CIA, loss of bone integrity and damage were clearly visible at vehicle and 5K-PEG-TRAIL treated mice. However, the paws of 30K-PEG-TRAIL treated mice showed no evidence of bone erosion and appeared similar to those of normal mice. The effects of 30K-PEG-TRAIL on joint inflammation were observed by conducting histological investigations of knee joints after H&E staining.

As compared with the clean, typical joint morphology observed in the normal mice, histological examination of CIA and 5K-PEG-TRAIL treated mice showed synovial hyperplasia, inflammatory cell infiltration, pannus formation, cartilage destruction, and bone erosion, which are all characteristics of RA. However, a weekly dose of 30K-PEG-TRAIL clinically reduced joint inflammation.

Example 5

30K-PEG-TRAIL Reduces Systemic Inflammation and Humoral Immunity in CIA

Materials and Methods

Animals from Example 4 were examined at the end of treatment. To determine cytokine levels in vivo, serum samples were collected from mice by aspirating retro-orbital blood. All samples were stored at −70° C. until used. Serum levels of pro-inflammatory cytokines of TNF-α, interleukin op-1-β, IL-2, and interferon-gamma (IFN-γ) were determined using a Bio-Plex suspension array system (Bio-Rad laboratories, Hercules, Calif.), according to the manufacturer's instructions. To measure collagen-specific autoantibodies levels in vivo, collected serum samples were analyzed using enzyme-linked immunosorbent assay (ELISA) kits (Chondrex) for CII-specific IgG1 and IgG2a antibody levels.

Results

The effects of 30K-PEG-TRAIL on systemic inflammation were investigated by measuring serum pro-inflammatory cytokine levels. The serum levels of TNF-α in 30K-PEG-TRAIL treated mice were 75% lower than those in CIA mice ($p<0.05$). Similar results were observed for IL-1β, IFN-γ, and IL-2 (67%, 55%, 60%, respectively, vs. non-treated CIA mice, $p<0.05$). These results indicate that reduced levels of pro-inflammatory cytokines in blood are related to the therapeutic effects of 30K-PEG-TRAIL on CIA, such as reduced inflammatory cell infiltration and edema.

Figure 4A:
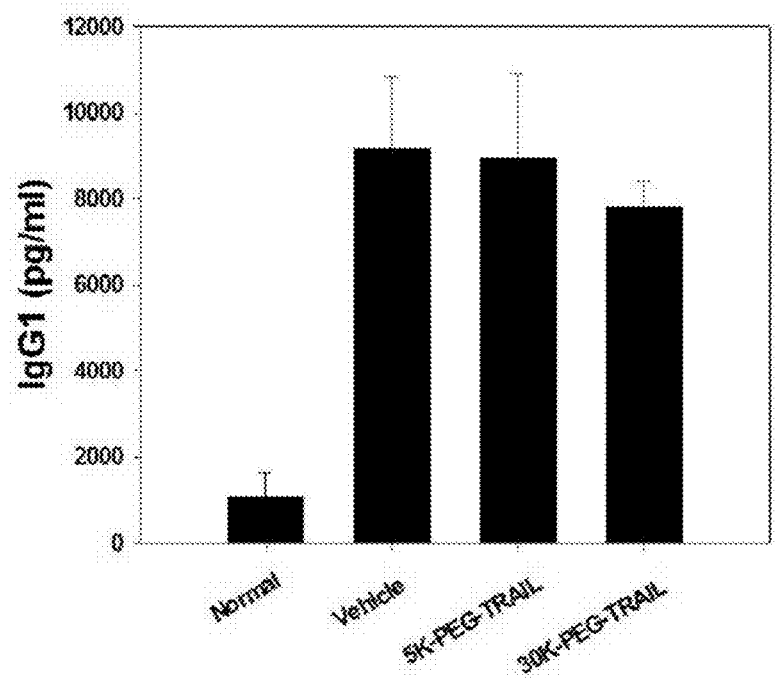
FIGS. 4A and 4B are bar graphs showing effects of vehicle, 5K-PEG, and 30K-PEG TRAIL analog treatment on the production of bovine type II collagen (CII)-specific antibodies IgG1 (A) and IgG2a (B) in the sera of CIA mice, and compared to sera of normal mice. Serum samples were collected from normal and vehicle-treated controls (CIA) or mice treated with doses of PEG-TRAIL analogs (300 µg/mouse/weekly injection) at 41 days post-CI. Data are expressed as means±SEMs (n=10 per group). **p<0.01 versus CIA mice.
Figure 4B:
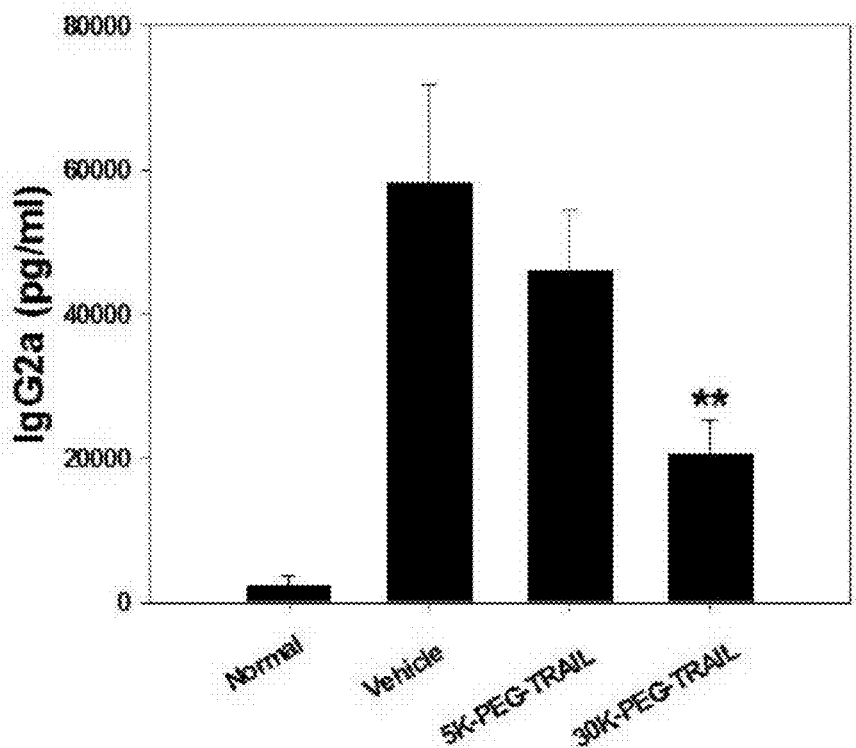

Humoral immunity against CII also plays an important role in the immunopathology of autoimmune arthritis, and CIA is also accompanied by high levels of circulating auto antibodies, which initiate joint inflammation (De Clerck, *Clinical rheumatology* 14 Suppl 2:14-8 (1995)). In particular, Th1-type IgG2a subclass antibody activates the complement cascade and plays a crucial role in the development of RA. 30K-PEG-TRAIL also affected humoral immune response, representing serum antibody levels, against CII. As illustrated in FIGS. 4A and 4B, the levels of CII-specific autoantibodies were barely detectable in the sera of normal mice, but were markedly elevated after two CII immunizations. No significant differences were observed between the serum levels of anti-CII IgG1 in CIA mice treatment with PEG-TRAIL analogs and CIA mice (FIG. 4A). However, anti-CII IgG2a levels were significantly reduced by 30K-PEG-TRAIL by 64.7% as compared with CIA mice, respectively (FIG. 4B). These results indicated that 30K-PEG-TRAIL reduced the productions of CII-specific autoantibodies in humoral immune response to secondary immunization.

Example 6

A combination of 5K-PEG-TRAIL and TNF-α blocker, Adalimumab (Humira®), Ameliorates Rheumatoid Arthritis Materials and Methods To investigate the effect of the combination of 5K-PEG-TRAIL and TNF-α blocker on the development and progression of arthritis, collagen-induced arthritis (CIA) DBA/1J mice were examined after i.p. administration of vehicle, 5K-PEG-TRAIL (300 μg/mouse/injection), adalimumab (50 μg/mouse/injection) or a combination of 5K-PEG-TRAIL (300 μg/mouse/injection) and adalimumab (50 μg/mouse/injection) every 3 days for 4 times in 2 weeks starting at Day 28 after immunization. Therapeutic effects were continuously monitored.

Results

Figure 5A:
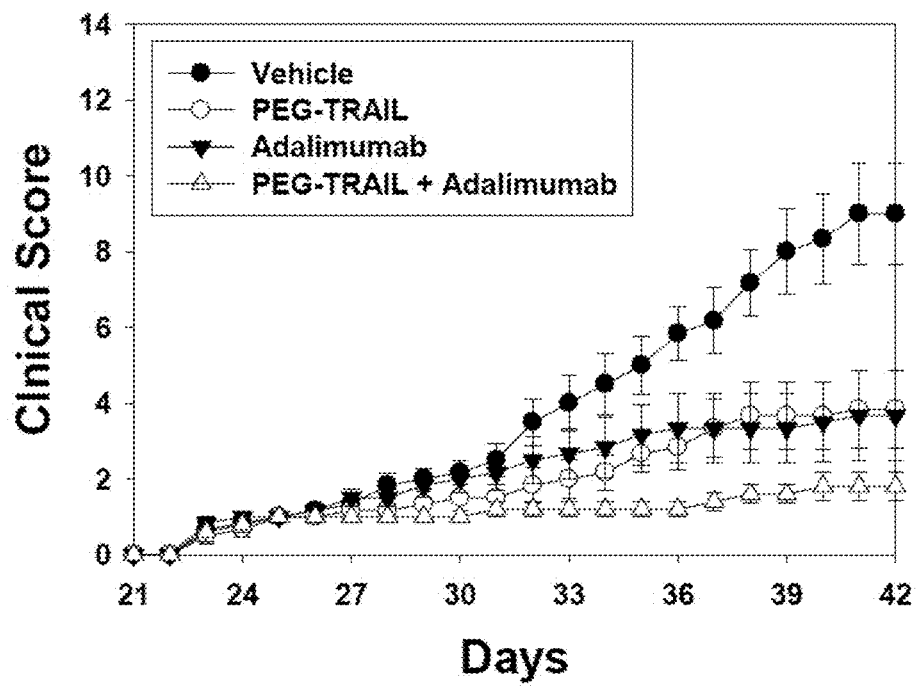
FIG. 5A is a line graph showing change in clinical score over time (days) in CIA mice treated with vehicle (●), 5K-PEG-TRAIL (300 µg/mouse/injection) (○), adalimumab (50 µg/mouse/injection) (▼) or a combination of 5K-PEG-TRAIL (300 µg/mouse/injection) and adalimumab (50 µg/mouse/injection) (Δ).
Figure 5B:
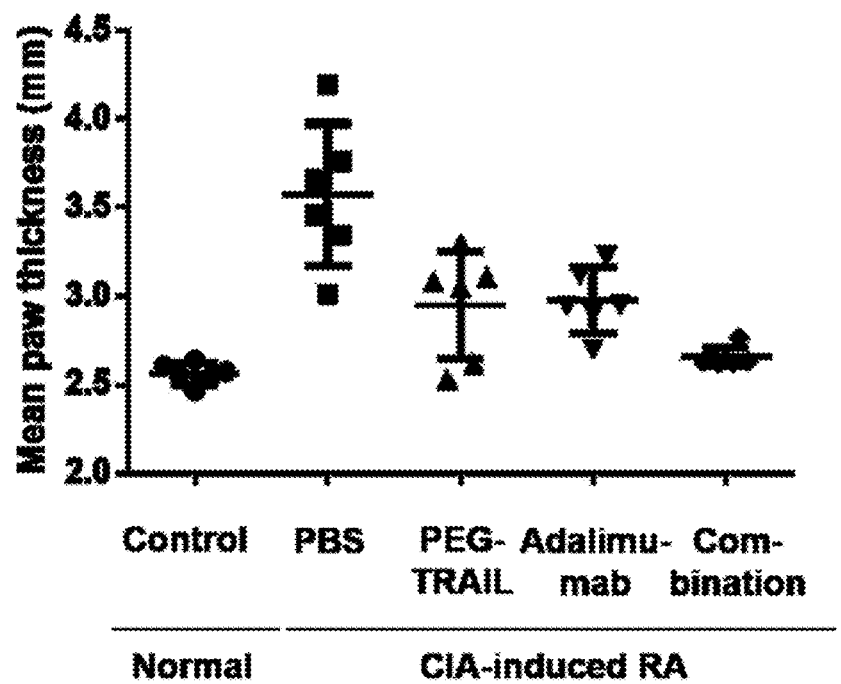
FIG. 5B is a dot plot of mean paw thickness (mm) for control, PBS, PEG-TRAIL, Adalimumab, or PEG-TRAIL in combination with Adalimumab from FIG. 5A.

5K-PEG-TRAIL showed efficacy similar to that of adalimumab when administered alone. When combined, 5K-PEG-TRAIL and adalimumab offered a significantly improved therapeutic effect (clinical scores for vehicle, 5K-PEG-TRAIL, adalimumab, combination; 9±1.34, 3.8±1.01, 3.6±1.20, and 1.8±0.37) (FIG. 5A). In particular, animal-to-animal variation of mean paw thickness was narrowed in the case of combination vs. drug alone (FIG. 5B).

We claim:

1. A method of treating rheumatoid arthritis comprising systemically administering a tumor necrosis factor-related apoptosis-inducing ligand (TRAIL) conjugate to a subject with rheumatoid arthritis by injection twice a week, once a week, once every two weeks, or about once every 28 days, in an amount between 1 mg/kg and 100 mg/kg effective to increase apoptosis of pro-inflammatory immune cells and increase the quantity of anti-inflammatory Foxp3+regulatory T cells (Treg), wherein the TRAIL-conjugate comprises a TRAIL polypeptide comprising amino acids 114-281 of SEQ ID NO:1 fused to a multimerization domain that allows trimerization, where the fusion polypeptide is conjugated to polyethylene glycol (PEG) or a derivative of PEG, wherein the PEG or the derivative thereof has a molecular weight between 5,000 and 60,000 Da.

2. The method of claim 1 wherein administration of the TRAIL-conjugate reduces joint swelling, erythema, joint rigidity, and/or inflammatory cell infiltration into the joint(s).

3. The method of claim 1 wherein the TRAIL-conjugate reduces expression or circulating levels of one or more inflammatory or pro-inflammatory molecules selected from the group consisting of ICAM-1, COX-2, iNOS, TNF-α, IL-1β, IFN-γ, IL-2, IL-6, IL-17, and combinations thereof, which are elevated in rheumatoid arthritis.

4. The method of claim 1 wherein the TRAIL-conjugate increases the expression or circulating levels of anti-inflammatory cytokines TGF-β or IL-10, or combination thereof.

5. The method of claim 1 wherein the PEG or the derivative thereof has a molecular weight at least 30,000 Da.

6. The method of claim 1 wherein the subject does not have cancer.

7. The method of claim 1 comprising administering to the subject an agent which reduces the expression or circulation of a pro-inflammatory molecule TNF-α.

8. The method of claim 7 wherein the agent is selected from the group consisting of etanercept, infliximab, adalimumab, golimumab, and certolizumab pegol.

9. The method of claim 1 wherein the fusion polypeptide of the TRAIL-conjugate is linked to the polyethylene glycol molecule or the derivative thereof via a linker.

10. The method of claim 1 wherein the multimerization domain comprises a zipper motif.

11. The method of claim 10 wherein the zipper motif is an isoleucine zipper motif.

12. The method of claim 1 wherein the polyethylene glycol derivative is selected from the group consisting of methoxypolyethylene glycol succinimidyl propionate, methoxypolyethylene glycol N-hydroxysuccinimide, methoxypolyethylene glycol aldehyde, methoxypolyethylene glycol maleimide, and multiple-branched polyethylene glycol.

13. The method of claim 1 wherein the TRAIL-conjugate is administered in a dosage of between 5 and 50 mg/kg, or between 10 and 20 mg/kg.

14. The method of claim 1 wherein the TRAIL-conjugate is administered in a dosage between 40 and 60 mg/m$^2$ or about 45 mg/m$^2$.

* * * * *

SEQUENCE LISTING

```
<160> NUMBER OF SEQ ID NOS: 27

<210> SEQ ID NO 1
<211> LENGTH: 281
<212> TYPE: PRT
<213> ORGANISM: Homo sapiens

<400> SEQUENCE: 1

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175
```

```
His Glu Lys Gly Phe Tyr Tyr Ile Tyr Ser Gln Thr Tyr Phe Arg Phe
                180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
                260                 265                 270

Ser Phe Phe Gly Ala Phe Leu Val Gly
        275                 280

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide - FLAG tag

<400> SEQUENCE: 2

Asp Tyr Lys Asp Asp Asp Asp Lys
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide - haemagglutinin tag

<400> SEQUENCE: 3

Tyr Pro Tyr Asp Val Pro
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide - MYC tag

<400> SEQUENCE: 4

Ile Leu Lys Lys Ala Thr Ala Tyr Ile Leu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Glu Gln Lys Leu Ile Ser Glu Glu Asp Leu
1               5                   10

<210> SEQ ID NO 6
<211> LENGTH: 19
<212> TYPE: DNA
<213> ORGANISM: Artificial Sequence
<220> FEATURE:
```

```
<223> OTHER INFORMATION: Synthetic Primer

<400> SEQUENCE: 6
cagcaacagc aaggcgaaa                                                    19

<210> SEQ ID NO 7
<211> LENGTH: 21
<212> TYPE: DNA
<213> ORGANISM: Artificial Sequence
<220> FEATURE:
<223> OTHER INFORMATION: Synthetic Primer

<400> SEQUENCE: 7
ctggacctgt gggttgttga c                                                 21

<210> SEQ ID NO 8
<211> LENGTH: 18
<212> TYPE: DNA
<213> ORGANISM: Artificial Sequence
<220> FEATURE:
<223> OTHER INFORMATION: Synthetic Primer

<400> SEQUENCE: 8
gtggcgggaa agttcctg                                                     18

<210> SEQ ID NO 9
<211> LENGTH: 23
<212> TYPE: DNA
<213> ORGANISM: Artificial Sequence
<220> FEATURE:
<223> OTHER INFORMATION: Synthetic Primer

<400> SEQUENCE: 9
cgtcttgcag gtcatcttag gag                                               23

<210> SEQ ID NO 10

<400> SEQUENCE: 10

000

<210> SEQ ID NO 11
<211> LENGTH: 24
<212> TYPE: DNA
<213> ORGANISM: Artificial Sequence
<220> FEATURE:
<223> OTHER INFORMATION: Synthetic Primer

<400> SEQUENCE: 11
agtagtcgca cactctgttg tgct                                              24

<210> SEQ ID NO 12
<211> LENGTH: 18
<212> TYPE: DNA
<213> ORGANISM: Artificial Sequence
<220> FEATURE:
<223> OTHER INFORMATION: Synthetic Primer

<400> SEQUENCE: 12
cctggtacgg gcattgct                                                     18

<210> SEQ ID NO 13
<211> LENGTH: 18
<212> TYPE: DNA
<213> ORGANISM: Artificial Sequence
<220> FEATURE:
```

<223> OTHER INFORMATION: Synthetic Primer

<400> SEQUENCE: 13
gctcatgcgg cctcctt                                                  18

<210> SEQ ID NO 14
<211> LENGTH: 28
<212> TYPE: DNA
<213> ORGANISM: Artificial Sequence
<220> FEATURE:
<223> OTHER INFORMATION: Synthetic Primer

<400> SEQUENCE: 14
cgacttcaac agcaactccc actcttcc                                      28

<210> SEQ ID NO 15
<211> LENGTH: 28
<212> TYPE: DNA
<213> ORGANISM: Artificial Sequence
<220> FEATURE:
<223> OTHER INFORMATION: Synthetic Primer

<400> SEQUENCE: 15
cgacttcaac agcaactccc actcttcc                                      28

<210> SEQ ID NO 16
<211> LENGTH: 24
<212> TYPE: DNA
<213> ORGANISM: Artificial Sequence
<220> FEATURE:
<223> OTHER INFORMATION: Synthetic Primer

<400> SEQUENCE: 16
tctcatgcac caccatcaag gact                                          24

<210> SEQ ID NO 17
<211> LENGTH: 24
<212> TYPE: DNA
<213> ORGANISM: Artificial Sequence
<220> FEATURE:
<223> OTHER INFORMATION: Synthetic Primer

<400> SEQUENCE: 17
accactctcc ctttgcagaa ctca                                          24

<210> SEQ ID NO 18
<211> LENGTH: 25
<212> TYPE: DNA
<213> ORGANISM: Artificial Sequence
<220> FEATURE:
<223> OTHER INFORMATION: Synthetic Primer

<400> SEQUENCE: 18
caaccaacaa gtgatattct ccatg                                         25

<210> SEQ ID NO 19
<211> LENGTH: 21
<212> TYPE: DNA
<213> ORGANISM: Artificial Sequence
<220> FEATURE:
<223> OTHER INFORMATION: Synthetic Primer

<400> SEQUENCE: 19
gatccacact ctccagctgc a                                             21

```
<210> SEQ ID NO 20
<211> LENGTH: 21
<212> TYPE: DNA
<213> ORGANISM: Artificial Sequence
<220> FEATURE:
<223> OTHER INFORMATION: Synthetic Primer

<400> SEQUENCE: 20
ggtgacaacc acggccttcc c                                              21

<210> SEQ ID NO 21
<211> LENGTH: 25
<212> TYPE: DNA
<213> ORGANISM: Artificial Sequence
<220> FEATURE:
<223> OTHER INFORMATION: Synthetic Primer

<400> SEQUENCE: 21
ttaagcctcc gacttgtgaa gtggt                                          25

<210> SEQ ID NO 22
<211> LENGTH: 18
<212> TYPE: DNA
<213> ORGANISM: Artificial Sequence
<220> FEATURE:
<223> OTHER INFORMATION: Synthetic Primer

<400> SEQUENCE: 22
gctccgaagg ccctcaga                                                  18

<210> SEQ ID NO 23
<211> LENGTH: 19
<212> TYPE: DNA
<213> ORGANISM: Artificial Sequence
<220> FEATURE:
<223> OTHER INFORMATION: Synthetic Primer

<400> SEQUENCE: 23
ctttccctcc gcattgaca                                                 19

<210> SEQ ID NO 24
<211> LENGTH: 22
<212> TYPE: DNA
<213> ORGANISM: Artificial Sequence
<220> FEATURE:
<223> OTHER INFORMATION: Synthetic Primer

<400> SEQUENCE: 24
tgacgtcact ggagttgtac gg                                             22

<210> SEQ ID NO 25
<211> LENGTH: 21
<212> TYPE: DNA
<213> ORGANISM: Artificial Sequence
<220> FEATURE:
<223> OTHER INFORMATION: Synthetic Primer

<400> SEQUENCE: 25
ggttcatgtc atggatggtg c                                              21

<210> SEQ ID NO 26
<211> LENGTH: 22
<212> TYPE: DNA
<213> ORGANISM: Artificial Sequence
<220> FEATURE:
<223> OTHER INFORMATION: Synthetic Primer
```

```
<400> SEQUENCE: 26
atttgaattc cctgggtgag aa                                              22

<210> SEQ ID NO 27
<211> LENGTH: 25
<212> TYPE: DNA
<213> ORGANISM: Artificial Sequence
<220> FEATURE:
<223> OTHER INFORMATION: Synthetic Primer

<400> SEQUENCE: 27
acaccttggt cttggagctt attaa                                           25
```